(12) United States Patent
Ganiban et al.

(10) Patent No.: US 11,266,395 B2
(45) Date of Patent: Mar. 8, 2022

(54) DEVICES AND METHODS TO PROVIDE HANDS FREE SCLERAL DEPRESSION DURING OPHTHALMIC PROCEDURES

(71) Applicants: Gary Ganiban, Merritt Island, FL (US); Michael W. Calhoun, Lighthouse Point, FL (US)

(72) Inventors: Gary Ganiban, Merritt Island, FL (US); Michael W. Calhoun, Lighthouse Point, FL (US)

(73) Assignee: Ganihand, LLC, St. Lighthouse Point, FL (US)

( * ) Notice: Subject to any disclaimer, the term of this patent is extended or adjusted under 35 U.S.C. 154(b) by 615 days.

(21) Appl. No.: 14/741,868

(22) Filed: Jun. 17, 2015

(65) Prior Publication Data
US 2015/0359529 A1    Dec. 17, 2015

Related U.S. Application Data

(60) Provisional application No. 62/013,326, filed on Jun. 17, 2014, provisional application No. 62/042,549, filed on Aug. 27, 2014, provisional application No. 62/114,848, filed on Feb. 11, 2015.

(51) Int. Cl.
| | | |
|---|---|---|
| *A61F 9/007* | (2006.01) | |
| *A61B 17/02* | (2006.01) | |
| *A61F 9/00* | (2006.01) | |
| *A61B 90/30* | (2016.01) | |
| *A61B 17/00* | (2006.01) | |

(52) U.S. Cl.
CPC ...... *A61B 17/0231* (2013.01); *A61B 17/0293* (2013.01); *A61B 90/30* (2016.02); *A61F 9/007* (2013.01); *A61F 9/0008* (2013.01); *A61B 2017/00398* (2013.01); *A61B 2017/00557* (2013.01); *A61B 2017/00893* (2013.01); *A61B 2017/0212* (2013.01); *A61B 2017/0287* (2013.01)

(58) Field of Classification Search
CPC ..... A61B 17/0231; A61F 9/007; A61F 9/0008
See application file for complete search history.

(56) References Cited

U.S. PATENT DOCUMENTS

| | | | |
|---|---|---|---|
| 6,083,155 A | 7/2000 | Trese | |
| 2003/0139808 A1 | 7/2003 | Shahinpoor et al. | |
| 2004/0204727 A1* | 10/2004 | Olsen | A61B 17/0231 606/166 |

(Continued)

OTHER PUBLICATIONS

International Search Report, PCT/US2015/036152, dated Sep. 16, 2015, 2 pages.

*Primary Examiner* — Leslie Lopez
(74) *Attorney, Agent, or Firm* — Michael J. Keller

(57) ABSTRACT

The devices and methods of the present invention provide a means to depress the sclera in such a fashion as to provide single point, multiple point, semicircular or 360° circumferential scleral tissue depression without the need for manual manipulation of the scleral depressor. The device comprises a shaped depressor for insertion between the sclera and the orbit of the eye and a holding means for positioning the depressor. In some embodiments the device can be integrated with a speculum. Use of the device eliminates the need to have a second person manipulate the depressor during the procedure and directly enables bimanual surgery.

15 Claims, 11 Drawing Sheets

(56) References Cited

U.S. PATENT DOCUMENTS

2008/0243139 A1 10/2008 Dusek
2010/0004499 A1* 1/2010 Brigatti ................ A61N 5/1017
600/7

* cited by examiner

DEVICES AND METHODS TO PROVIDE HANDS FREE SCLERAL DEPRESSION DURING OPHTHALMIC PROCEDURES

PRIORITY CLAIM AND INCORPORATION BY REFERENCE

This application claims priority to U.S. provisional application No. 62/013,326 filed on Jun. 17, 2014, U.S. provisional application No. 62/042,549 filed on Aug. 27, 2014 and to U.S. provisional application No. 62/114,848 filed on Feb. 11, 2015; the contents of which are expressly incorporated by reference. All references cited herein are expressly incorporated into the specification by reference.

FIELD OF THE INVENTION

The invention is generally directed to devices and methods for use in providing hands free scleral depression. Scleral depression is generally required for ophthalmic related surgical procedures and requires a scleral depressor to be manipulated by hand.

BACKGROUND OF THE INVENTION

Scleral depression, also known as scleral indentation, is a method of depressing the peripheral fundus of the ocular globe so the peripheral (retinal) tissue is visible directly through the pupil of the patient's eye. Typically, scleral depression is performed during ophthalmic surgical procedures in conjunction with a Binocular Indirect Ophthalmo Microscope (BIOM) and an operating microscope to provide the surgeon with a better, more direct view to perform ophthalmic procedures such as a vitrectomy, retinal reattachment via laser and other procedures which require a direct view of the retina.

The ocular globe is pressed by placing a tool between the globe and the orbit of the eye, generally referred to as the fornix, and having someone hold the tool in position. The problem, there is limited geography to allow any hand other than the surgeons in the space around the eye. Additionally, if a second person is hold the tool, there may be coordination issues.

There is a need in the art for a device which remains in the desired position and allows a single person to depress the sclera in a hands free manner and carry out the observation or other procedures.

SUMMARY OF THE INVENTION

Devices and methods for providing hands free scleral depression during ophthalmic procedures have been developed. These devices and methods include providing hands free single point, multiple point, semicircular (180° or less) or circumferential (360°) scleral depression in superior, inferior, nasal and temporal ophthalmic anatomical locations. These devices will enable bimanual retinal surgical techniques by reducing or eliminating the need for a surgeon to use one hand, or a surgical assistant to aid in scleral depression without interfering with other instruments in the surgical field, for example ports, infusion lines, light pipes, lasers and other devices commonly used during surgery. These devices may provide scleral depression independent of, or be integral to a fixed, or adjustable lid speculum devices.

In one embodiment, the device is ring like and is designed to sit directly around the eye, encircling the anterior globe region after placement of a lid speculum. The design of the ring accommodates single or multiple commonly available scleral depressors such that the ring holds the depressors in a desired position to provide hands free scleral depression. The weight of the ring provides positional stability for the depressors to remain in a desired position within the fornix so as to provide scleral depression without the use of hands. In addition, scleral depression may be provided at one point, or at multiple points along the circumference of the ring by providing single or multiple points to hold the scleral depressor(s). In the example of a single point scleral depression, the position of depression is easily adjustable by lifting the ring, rotating to the desired position and replacing the depressor within the fornix.

In another embodiment, a spring like element is integrated into the lid speculum and, once the lid speculum is in place, allows for a scleral depressor to be used by positioning within the desired location of the fornix and then engaging the scleral depressor into the spring like element via a press fit into the spring coils. This arrangement allows for scleral depression to occur at a single point anywhere along the 360° circumferential range of the device. In addition, the device can provide for simultaneous multiple points of scleral depression along the 360° circumferential range of the device by engagement of more than one scleral depressor within the device. The angular and depth positions of the scleral depressor are also easily adjustable. The device can also be constructed to provide less than 360° degree capability. This arrangement may be fabricated to work with any lid speculum. It is also worth noting that this spring like element may also aid in the accommodation of infusion lines such that the lines are securely held in place prior to entering the sclera.

In another embodiment, the design is based on use of a flexible member designed for insertion into the fornix, with the ability to provide a 360°, or less, depression of the peripheral fundus. This flexible member is constructed so that it may be delivered over the outer diameter of the globe, within the fornix, with or without a delivery tool. The length of the flexible member may be specifically designed to provide a particular degree of scleral depression including all, or a portion of the circumference. The profile of the flexible member may be designed to optimize grip on the globe while remaining autraumatic. The diameter of the flexible member is controlled by design to deliver the desired scleral depression and the device is easily removable from the fornix.

In yet another embodiment, the design is based on a device designed to be selectively inflated by either hydrostatic or pneumatic pressure. The device is placed into the fornix and the inflation adjusted such that the desired level of depression is provided. This design has the ability to provide a single point, multiple points, semicircular or circumferential depression. This device may also contain an outer, external member intended to restrict the inflation such that the outer diameter does not increase, but rather the inner diameter decreases to a point at which the desired level of scleral depression is provided. In addition, this device may include a member internal to the inflatable element that serves to provide structure to the inflatable member and assist in placement of the device within the fornix. This member may also serve to provide structural support to the inflatable element during the procedure and will also facilitate removal of the device from the fornix.

In yet another embodiment, the device may be constructed of a member designed to provide a single point, multiple points, semicircular or circumferential scleral depression capability. This member may be specifically designed to transition from a compressed state to an expanded state via reaction to the selective introduction of fluid. One example would be a member, in a compressed state, which is covered with a thin, fluid barrier membrane. Once the member is positioned within the fornix, fluid may be injected through the membrane directly into the member. The member would then expand with the introduction of fluid and provide the desired level of scleral depression.

In yet another embodiment, the device may be constructed of a member designed to provide a single point, multiple points, semicircular or circumferential scleral depression capability. This member may be constructed of metallic, polymer or any other suitable materials or combinations thereof. The profile, or cross sectional shape, of the portion of the device contacting the sclera may be designed to optimize contact with the surface of the sclera. This design may provide for the ability of the user to adjust the level of scleral depression as needed during the procedure.

In yet another embodiment, the device may be constructed of a modified speculum which is enabled to interface with a depression element configured to provide hands free scleral depression in a single point, multiple point, semicircular or circumferential fashion. This interface is designed to allow the user to position the scleral depression element within the fornix and then attach to the lid speculum. This attachment serves to maintain position of the scleral depression element within the fornix. The depression element is adjustable at various points along the lid speculum and one or more than one depression element may be used to provide scleral depression.

In yet another embodiment, the device may be constructed of a member designed to be held in place by insertion of a feature under or in a portion of a lid speculum. Insertion of this feature serves to stabilize the scleral depression device within the fornix such that hands free depression is provided. The degree of depression can be controlled by the distance of the feature from the depression element, design of the depression element or a combination. The depression element may be fixed, changeable or inflatable. It may also be possible to design the feature such that the distance from the depression element is adjustable by the user.

In yet another embodiment, the device may be constructed in a similar manner as an adjustable lid speculum such that one arm of the adjustable lid speculum provides a scleral depression element with, single point, multiple point, semicircular or circumferential depression, and the other arm of the adjustable lid speculum attaches to the lid speculum in use. This attachment point serves to provide leverage for obtaining scleral depression. Once the device is in place, the level of scleral depression can be adjusted by opening or closing the speculum adjustment mechanism. This configuration can also be designed so that both arms fit into the fornix such that the majority of the globe is depressed as the device is adjusted and scleral depression is provided in a double semicircular, or other selective range manner. This design may or may not be fabricated to interface with a lid speculum.

In yet another embodiment, the devices as described above may contain a feature that provides for the ability of light to be transmitted from the device onto the outer surface of the sclera. This light would be visible from inside the globe of the eye, through the sclera and may originate from a lighting feature attached to the device, or may originate from a transmission of light through the device itself. The light source may be provided by a self-contained, wireless and/or wired mechanism and may additionally use batteries, direct electrical current or a combination thereof. The light source may utilize commonly available components, including light emitting diodes.

In yet another embodiment, these scleral depression elements may be designed such that they have the capability to be loaded with a particular pharmaceutical. This loading of medication is intended to serve as a drug delivery mechanism within the fornix. The element may be loaded with the desired drug either prior to, or after placement into the fornix. Once the element is placed within the fornix, drug would be delivered directly into the surrounding tissue during the time the element is in place. This design may be fabricated with the capability to internally contain a liquid compound and dispense the material directly into the fornix over a desired time period. There may also be a feature that provides for the capability to re-load the depression element with additional compound. An additional embodiment of the drug delivery design may also be fabricated such that the depression element is coated with a particular drug intended to be delivered from the outside of the depression element directly into the fornix. Both the internal and external delivery concepts may be configured to deliver single, and multiple compounds within the fornix in a single or time released dosage. These compounds may include any pharmaceuticals currently used in ophthalmic surgery for antiseptic, pain or other typical ophthalmic applications.

Additionally, there is an embodiment in which, as one example, the compliant member design may be combined with electro-mechanical features so as to allow for automated operation of the device. In the compliant member example, the filament which serves as the member to provide a means to reduce the diameter of the compliant member would be connected to a motor which would serve to move the filament in one direction or the other as needed to provide constriction or release of the compliant member. This motor would in turn be connected to a feedback mechanism that would take instructions from the user and translate them into movement of the motor. This feedback mechanism may be as complex as a computer or as simple as one or more switches. This mechanism may include some level of software in the more complex arrangement, or no software in the simplest arrangement. The feedback mechanism may also incorporate the ability to monitor the maximum and minimum dimensions of the compliant member and provide the user with feedback to indicate pressure, time, temperature, dimension or combination thereof for the scleral depression. In addition, the feedback mechanism may incorporate the ability for the user to have a hand or foot control which is remote to the device. This feature would give the use the ability to manipulate the device from inside or outside of the direct surgical field. The feedback mechanism may also be remote from the patient and connected wirelessly via Bluetooth, or other wireless protocol commonly used in a medical environment. The motor and/or feedback mechanism may be powered by direct electrical connection, battery supply or some combination thereof. It is anticipated that the configurations for power supply would contain materials and voltages/amperages as normally seen in a medical environment. It is anticipated that the motor component may be disposable or reusable, while the feedback and power mechanisms would likely be reusable. This automated configuration would also be adaptable to the hydrostatic or pneumatic concepts in a similar fashion as to the compliant member. Other hands free scleral depression concepts disclosed in this application may also be designed to work with this automated configuration.

BRIEF DESCRIPTION OF THE DRAWINGS

FIGS. 15A-B is a cross section of a scleral depressor.

DETAILED DESCRIPTION OF THE INVENTION

Figure 1A:
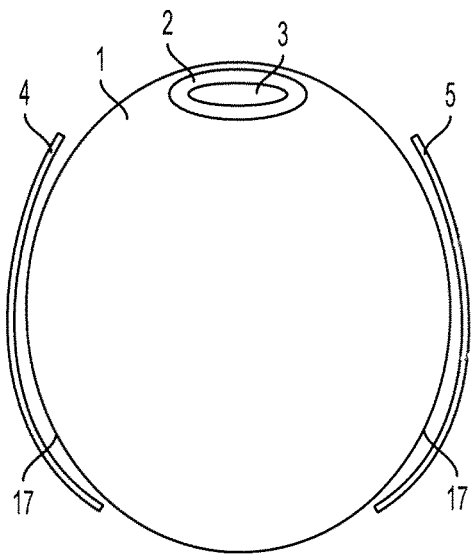
FIG. 1A is a drawing of a cross section of an eye.
Figure 1B:
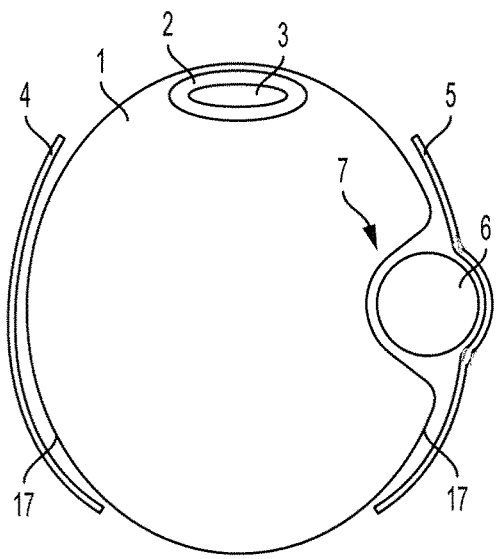
FIG. 1B is a cross section of an eye showing scleral depression.

Surgeons use indirect ophthalmoscopy through the lens 2 of the eye 1 and to a hand held diopter with single point scleral depression to depress the sclera to examine the peripheral retina 17. FIG. 1A is a depiction of an eye without the use of scleral depression. There are peripheral regions which cannot easily be observed by the surgeon. Depression of the sclera 17 as shown in FIG. 1B brings the peripheral retina 7 tissue into the field of view of the surgeon. FIG. 1B provides a detailed view of scleral depression performed on a human eye showing the effect on the inside and outside of the globe. In this example, the scleral depression is provided by a hand held single point such as a cotton tip applicator.

In many retinal surgical procedures, it is of particular advantage for the surgeon to have both hands free so that focus can be maintained on the surgical procedure verses concentration on scleral depression and the surgical procedure. This is commonly known as practicing bi-manual surgery. There are no known commercially available scleral depressors that provide hands free scleral depression capability for the surgeon during a procedure. In a typical retinal surgical procedure, there are times when the surgeon frequently requires a clear view of the peripheral retina. This is necessary to visualize the retinal vitreous interface for complete removal of the vitreous and to inspect for defects prior to surgery as well as assessment of post-surgical success. If a situation exists in which the peripheral retina requires treatment (i.e.; laser therapy to repair a retinal tear), it is of great benefit for the retinal surgeon to manipulate that anatomical location to provide the best direct visual orientation possible via scleral depression. In a typical example, the surgical assistant would use one hand to depress the appropriate peripheral retinal tissue into the desired field of view. Typically, while the assistant is working to provide the surgeon with the appropriate viewing perspective, the assistant is unable to see the same view as the surgeon. This makes assisting the surgeon very difficult as there is no visual feedback loop. One must keep in mind that depression of the tissue is required throughout the procedure and (in this example) the surgeon is required to maintain focus on tissue position while delivering interventional therapy. While use of an assistant relieves the surgeon of having to perform scleral depression, it requires that the assistant be in close proximity to the surgeon and crowds the surgical field. In addition, the surgeon must frequently ask the assistant to adjust the scleral depression so that the best view is maintained. There is a level of difficulty in communicating the desired scleral depression position to the person assisting the surgical procedure. It is also worth noting that these instruments are designed to be used in typical surgical procedures to provide scleral depression without interfering with other instruments in the surgical field, for example ports, infusion lines, light pipes, lasers and other devices commonly used during surgery.

In addition to use in a surgical procedure, the instrument designs detailed in this application are also well suited for use in performing in office diagnosis requiring scleral depression as well as out-patient procedures.

In a typical operating room set up with the surgeon working on the patient's eye while an assistant passes instruments there are significant operating field space limitations.

Figure 2:
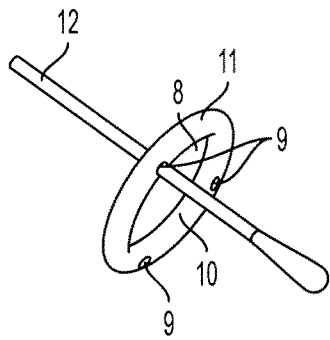
FIG. 2 is a drawing showing a solid ring embodiment of a scleral depressor relying on swabs for depression.

Referring to FIG. 2, the scleral depressor 8 is a ring shaped device having an inside diameter 10 and an outer diameter 11. The scleral depressor is shaped to fit around the perimeter of the eye between the eye 1 and the walls of the orbit 4, 5. The depressor is sized to be fully inserted into the fornix. There is at least one hole 9 in the ring through which a depressor 12 can be inserted. In this embodiment the probe is frequently a cotton swab or a Schocket. The scleral depressor 8 is positioned around the eye 1 and the depressor 12 used to push the sclera 17 to show peripheral retina 7.

The ring embodiment can further have a flat cross section ring with a holding element capable of infinite adjustment along the circumference of the ring. The holding element is designed such that there is a serration within the element which corresponds to serrations on the scleral depressor such that the up and down travel of the scleral depressor can be adjusted. The holding element is kept in place on the ring via compression with the ring.

Figure 3A:
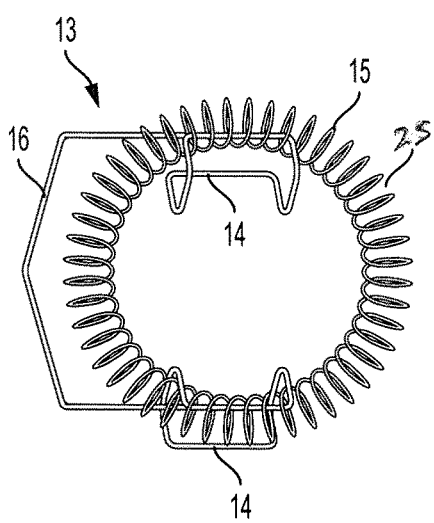
FIG. 3A is a spring embodiment of a scleral depressor mounted on an eyelid speculum.
Figure 3B:
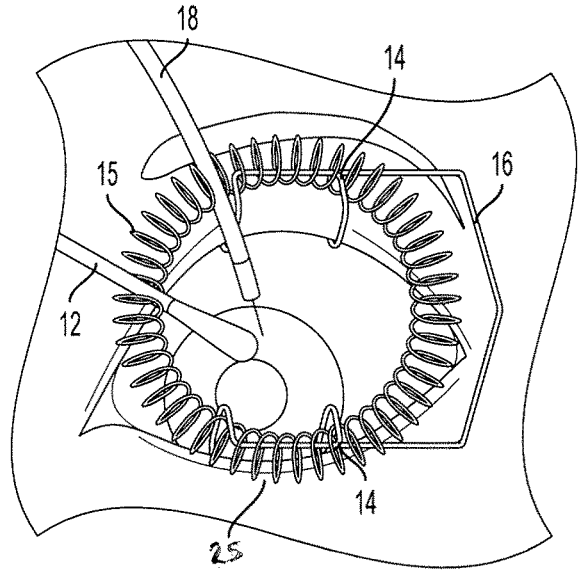
FIG. 3B is the scleral depressor of 3A positioned on an eye. An infusion line is also shown positioned within the spring embodiment.

Referring to FIG. 3A and FIG. 3B the annular concept is embodied in a spring like design with circumferential capability for depressor engagement mounted on a non-adjustable lid speculum. In this design the spring 15 has openings 25 for insertion of a depressor 12. The embodiment shown is mounted to an eyelid speculum 13 having a spring 16 acting on retractor elements 14. FIG. 3B depicts a depressor 12 (cotton tip applicator) and an infusion line 18 engaged within the eyelid speculum 13 mounted spring 15.

Figure 4:
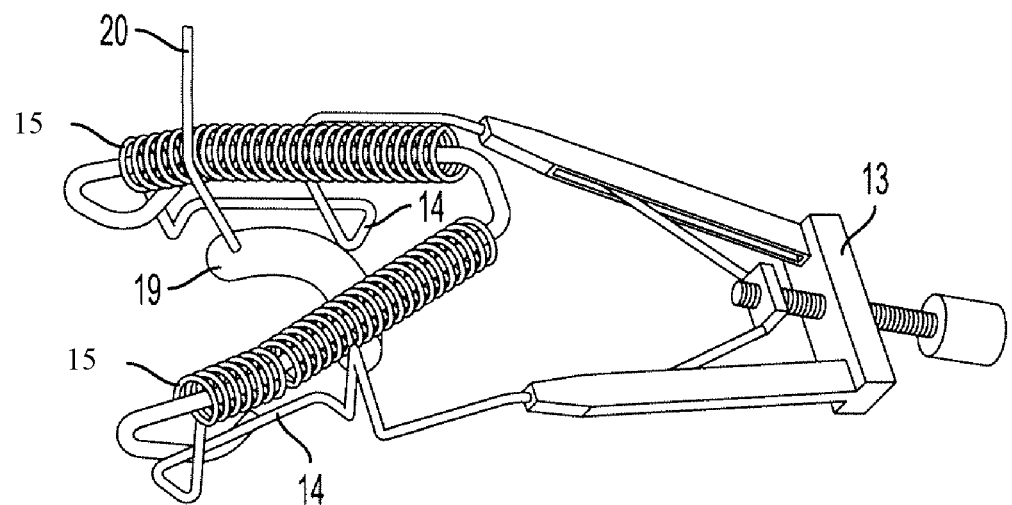
FIG. 4 is a drawing of another embodiment of a spring based scleral depressor mounted on an adjustable eyelid speculum.
Figure 13B:
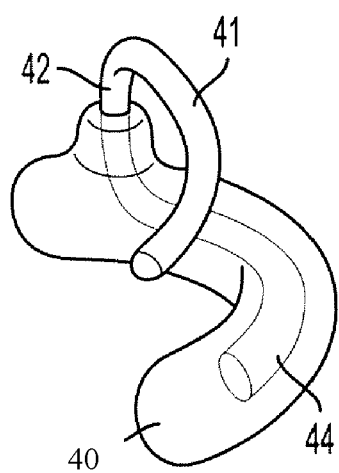
FIGS. 13A-D are drawings of a polymeric scleral depressor.

FIG. 4 depicts another spring like design on an adjustable lid speculum 13. In this embodiment the springs 15 are substantially linear and are positioned on the retractor 13. Openings 25 in the springs 15 allows for positioning of a depressor 19 by way of handle 20.

In another embodiment the ring is composed of a non-expandable outer ring lined with an expandable member which expands into the sclera. In this embodiment the assembly (coated with a fluid proof membrane) goes from a collapsed to an expanded state upon delivery of fluid or gas into the expandable member. Scleral depression is provided in the expanded state and can be controlled via the amount of fluid delivered as well as by the expansion characteristics of the expandable member.

Figure 5:
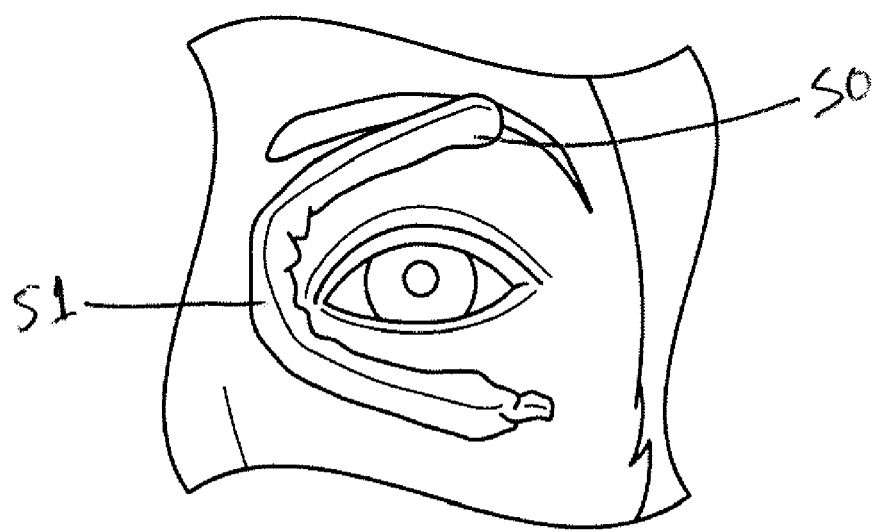
FIG. 5 is a coated expandable sponge embodiment of a scleral depressor

FIG. 5 depicts an expandable finger 51 concept contained within a fluid proof membrane 50. The finger 51 can have a non expanding surface and an expanding surface such that the expanding surface is positioned next to the eye and the non-expanding surface is position in the socket or the entire device can be expanding. Expansion can be provided by the injection of fluid or gas into the membrane 50. The core of the expandable finger 51 can include sponge or gel materials which swell upon injection of a fluid such as saline. The expandable finger 51 can be linear or curved and is designed to provide semicircular depression in approximate position on an eye model as shown in FIG. 5.

Figure 6:
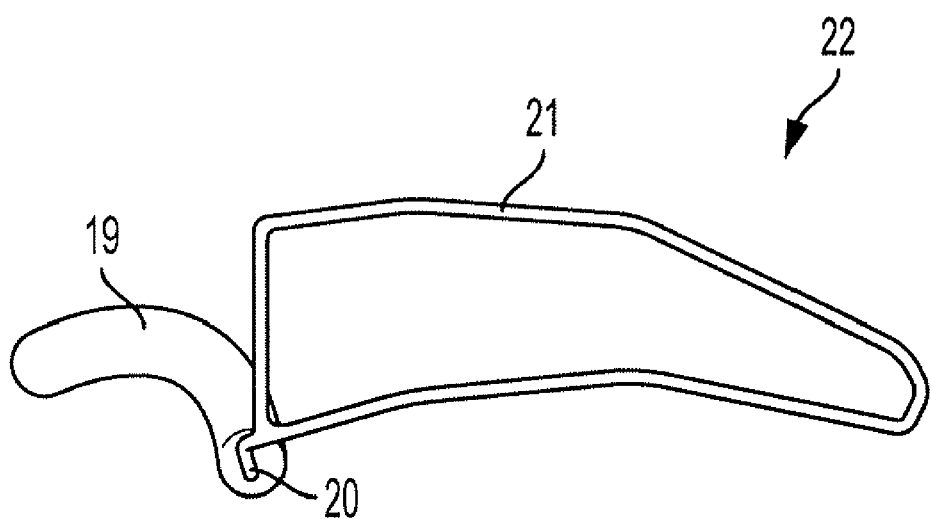
FIG. 6 is a stand alone version of a scleral depressor mounted on a handle.

FIG. 6 depicts a scleral depressor 22 as a stand-alone device comprised of a handle 21 and the depressor 19 connected by vertical arm 20. This embodiment would be positioned alone or in connection with a separate eyelid retractor.

The scleral depression can be provided a single point, semicircular or circumferential scleral depressors. It should be noted that several of these designs allow for the user to actively change the scleral depression element to alter the level of scleral depression, while maintaining the same underlying structural component. In one embodiment a circumferential scleral depressor has changeable scleral depression elements. These elements can be implemented circumferentially with changeable scleral depression elements in the approximate use position over an adjustable lid speculum. The depressor can be a semicircular scleral depressor with a depression element constructed of clear tubing, multiple depression elements comprised of at least one polymer bead or silicone present as beads or semicircular shapes. In one embodiment the arc covered by the depressor can be customized by the surgeon by using interchangeable sleeves or trimming a sleeve to the required dimensions. In some embodiments the position of the depressor is circumferentially adjustable in that the depressor can be positioned in different locations around the eye during the procedure.

Figure 7A:
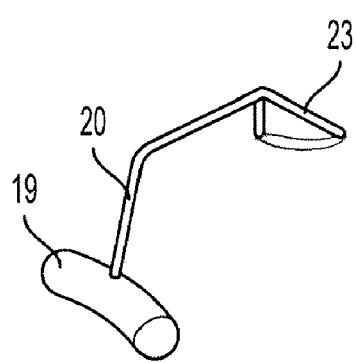
FIGS. 7A-D are solid scleral depressors.
Figure 7B:
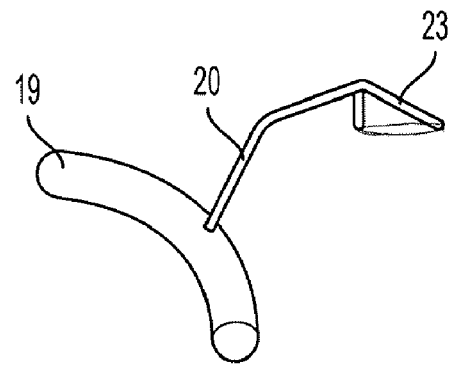
Figure 7C:
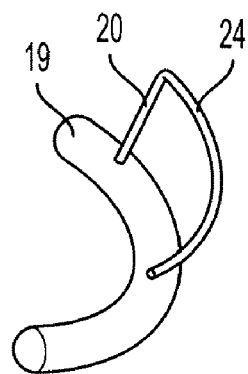
Figure 7D:
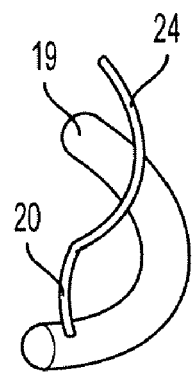
Figures 15, 15A:
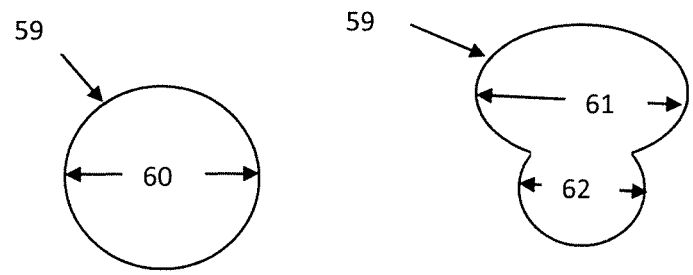

Referring to FIGS. 7A to 7D the solid scleral depression elements may be semicircular elements ranging from 0-360 degrees. 7A-D depict semicircular scleral depression elements 19 with multiple point scleral depression capability. The depressor 19 has handle 23 which are connected to the depressor with vertical arm 20. In some embodiments as shown in FIGS. 7C and 7D the handle is curved as shown by engagement arm 24 and runs approximately parallel to the depressor 19. In this embodiment the handle is designed to closely fit with an eyelid speculum as shown in FIG. 4. This engagement maintains the scleral depressor element within the fornix. The depression device will also function with a non-modified lid speculum. In this example, the depression element engagement arm is placed under the lid speculum. This fit provides stability and keeps the depression element in the desired location. FIG. 15A depicts a depressor with a constant diameter 60 in cross section 59 and FIG. 15B depicts a depressor having variable diameter cross section 59 having at least a diameter 61 and a diameter 62. The diameters can be made to any shape that will give the desired depression without causing damage to the eye or its socket. The cross section of the depressors 19 are preferably from about 2 mm to about 8 mm in thickness and 2 mm to about 8 mm in height with about 4-5 mm being most preferred for height and about 4-5 mm being most preferred for thickness. These cross sections may be designed to provide a specific depression profile. In a preferred embodiment the depressors cover an arc of 30 to 360 degrees, with 90180 degrees being preferred and 120 to 135 degrees being the most preferred range of arc of depression. The preferred vertical arm height 20 is from about 6 to about 14 mm with 8-12 mm being the most preferred height.

The devices of the present invention can be provided in a kit form having depressors 19 with a variety of diameters and lengths together with a means for holding at least one depressor in place.

In other embodiments the depressor of the present invention can be integrated into an adjustable eyelid speculum with one arm modified to act as a semicircular depression element. The other arm is modified such that engagement with a lid speculum is possible. It should be noted that this set up may also be modified to provide less semicircular depression, single or multiple point scleral depression, as well as circumferential scleral depression.

Figure 8:
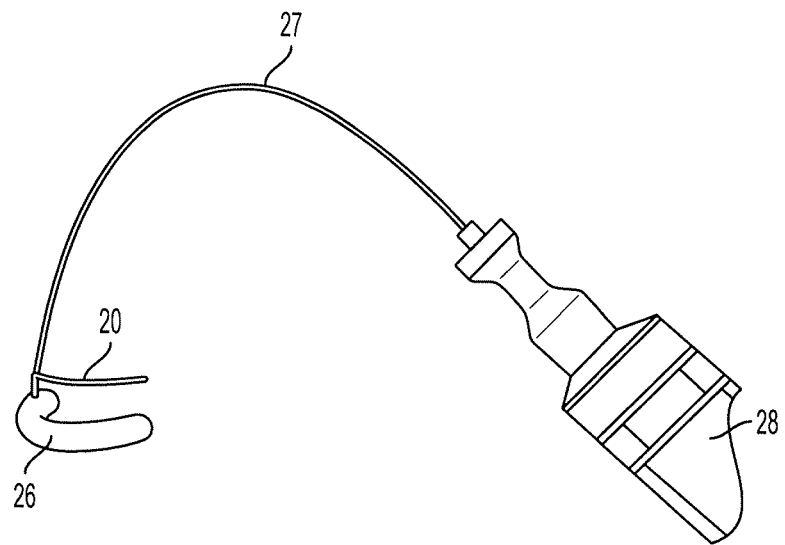
FIG. 8 is an inflatable scleral depressor.

FIG. 8 depicts an inflatable circumferential scleral depression device. The device consists of an inflatable depressor 26 having a deflated and an inflated state. Depressor 26 is connected to a pressure source 28 via tubing 27. The depressor 26 has handle 20 for positioning in or around an eyelid speculum to maintain positioning. This depressor may be inflated via pneumatic or hydrostatic pressure. Semicircular, single or multiple point depression is also possible with this design. The device may contain a rigid or semi rigid element inside the inflatable depressor to aid in positioning. In one embodiment the connections are made via Luer fittings and the pressure source is a syringe. The handle can be configured as a stand-alone device or to work with an eyelid speculum. This configuration can be designed to provide a wide range of scleral depression from the depression element by inflation using a hydrostatic or pneumatic source.

Figure 9:
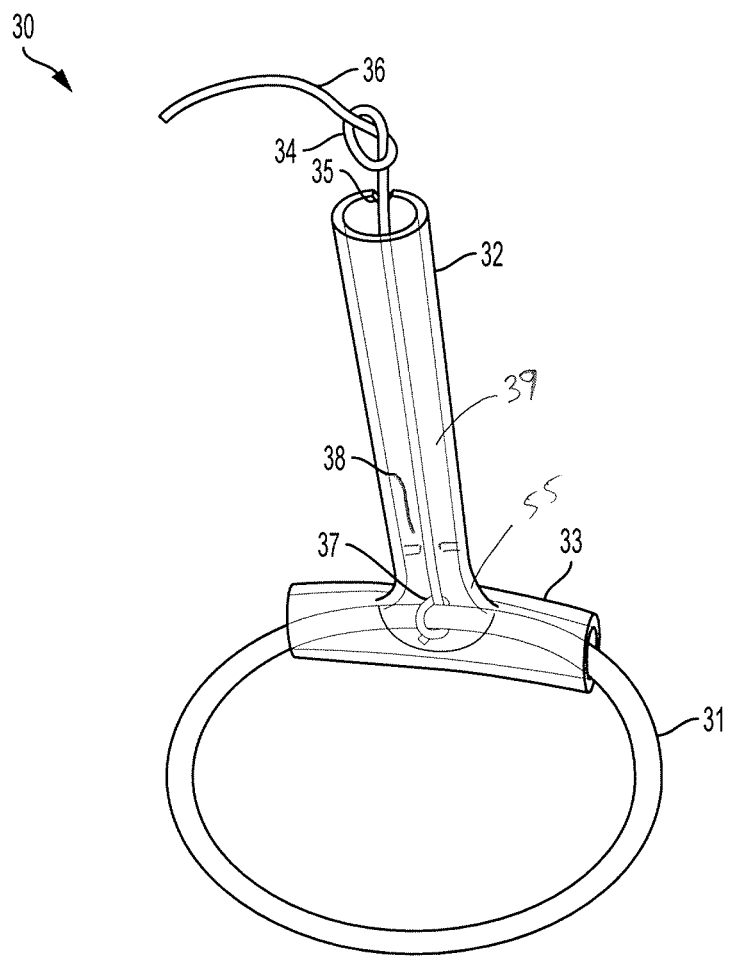
FIG. 9 is an embodiment of a scleral depressor having a loop for 360 degree depression.
Figure 10A:
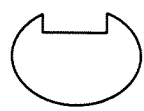
FIGS. 10A-L are various cross sectional shapes of a scleral depressor.
Figure 10B:
Figure 10C:
Figure 10D:
Figure 10E:
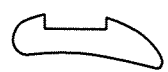
Figure 10F:
Figure 10G:
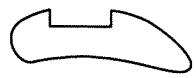
Figure 10H:
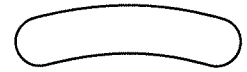
Figure 10I:
Figure 10J:
Figure 10K:
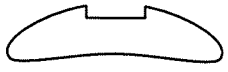
Figure 10L:
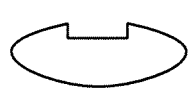
Figure 11A:
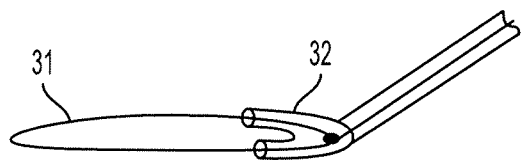
FIGS. 11A-B show the scleral depressor of FIG. 9 in an open and closed state.
Figure 11B:
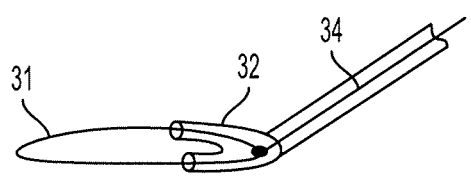

FIG. 9 depicts a compliant scleral depressor design 30 having a ring shaped compliant depressor 31 which extends to fit around the globe of an eye for delivery within the fornix of the eye. The device comprises a tubular housing having a hollow vertical member 32 which joins to a horizontal member 33. The two housings are preferably joined at a distal end of the vertical member 32 at a mid-point on the horizontal member 33 forming a hollow T shape having a lumen 37 through both the horizontal and vertical members. The compliant depressor element comprises an annular shaped band 31 disposed in the lumen of the horizontal member 33 of the housing. The compliant depressor element 31 is connected to an actuating element 36 inside joint of the lumen 35 by a fastening means 37. The fastening means can be any suitable means of fastening such as knots, adhesives, mechanical fasteners such as clamps, rivets, screws, etc. In one embodiment the compliant depressor element and the actuating element are comprised of a single piece of material. When the actuating element 36 is pulled, it pulls compliant depressor element 31 into the body of vertical housing member 32 thereby shortening the diameter of the ring. Restriction 38 in the lumen of vertical housing member 32 acts as a physical barrier to the compliant depressor element 31 preventing it from being pulled too tight around an eye. Actuating element 36 is locked in position using a locking means 35. In the simplest form the locking means comprises a knot 34 tied by the surgeon in the actuating element 36 which is positioned in a slit 35 at the end of vertical member 32. Actuating element 36 can have knots position at predetermined intervals either by tying, using adhesives or by molding to allow for preset positioning. Contemplated are the use of co-adhesives disposed on the exterior of the vertical member 32 and the exterior of actuating element 36 such that when the two elements are brought together the cohesives will securely hold the actuating element in position, yet would be separable to release it. In FIG. 11A the device is shown in an expanded state. In FIG. 11B the device is shown in a constricted position so as to provide circumferential scleral depression. When constricted a restriction 38 in lumen 39 prevents over constriction of the compliant member 31 by physically preventing the compliant member 31 from being pulled into the lumen 39 beyond the location of restriction 38. FIGS. 10A-10L depict several possible cross sectional profiles of the compliant member. The cross sections are preferably from about 2 mm to about 8 mm in thickness and 2 mm to about 8 mm in height with 5 mm being most preferred for height and 5 mm being most preferred for thickness. These cross sections may be designed to provide a specific depression profile. In a preferred embodiment the compliant member 31 is cut to release it to simplify removal.

Figure 14:
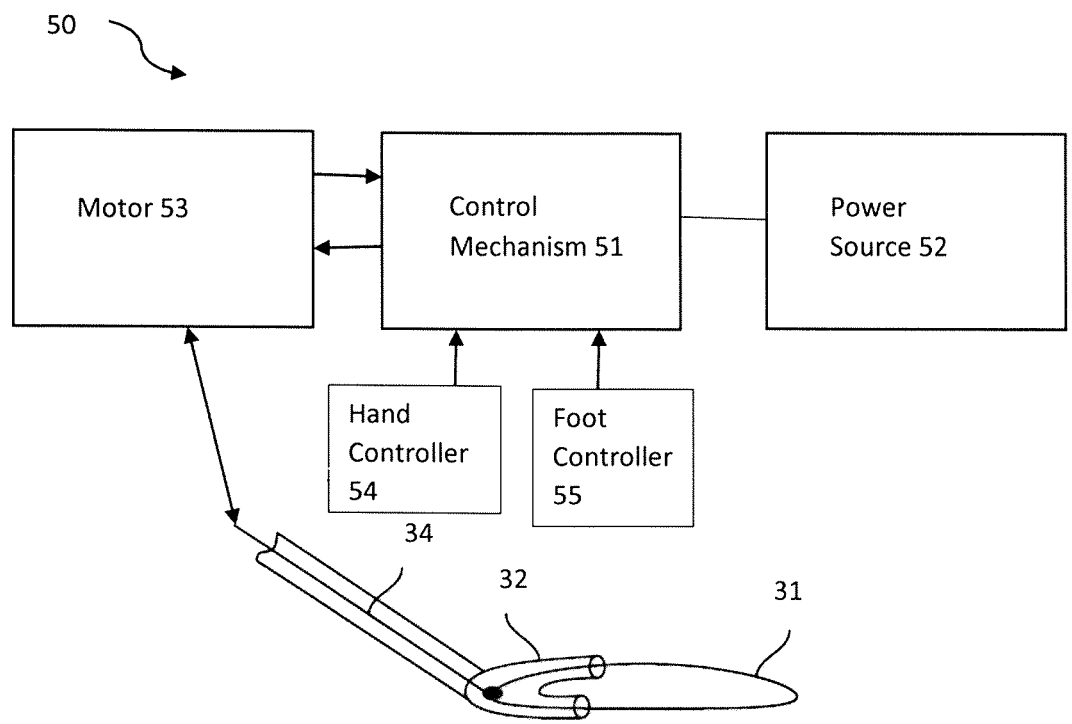
FIG. 14 is a diagram of a controller for an automated scleral depressor.

FIG. 14 depicts one of the hands free scleral depression concepts in an arrangement that provides the ability to electronically manipulate the device. In this embodiment the actuator element 34 is connected to motor 53. The motor 53 is connected to a control mechanism 51 which is connected to a power source 52. The control mechanism 51 can be digital or analog and serves to control the motor 53 base on the input from hand controller 54 and/or foot controller 55. The force from the motor acts on actuator element 34 which in turn applies or releases force on compliant member 31. The motor could be any suitable motor including piezo, dc, ac, servo linear and rotary motors capable of supplying enough torque. The motor could also be a hydraulic pump or gas compressor. In addition to the restriction 38, electronic safety measures could be implemented as torque or distance measurements to prevent too much force from being applied to the eye. Torque sensors could be incorporated into the compliant member 31 to sense the force applied to the eye.

This electromechanical device would allow the user to place the device and then operate it using a foot control, hand control or allow a person outside of the surgical field to manipulate the scleral depression device. This arrangement would potentially work with several embodiments of the hands free scleral depression concept.

In another embodiment the devices are disposable to prevent contamination from reuse or to prevent the use of a device which has exceeded its useful life.

Devices of the present invention may be made from any biocompatible materials including metals and polymers. The component parts may be made as separate pieces for assembly or made as one device. If the device is metal, it may be made using any conventional metalworking techniques including but not limited to stamping, forging, extruding, bending, drilling, sawing, sanding, a lathe, router or any combination thereof. Polymeric devices can be readily molded from one or more polymers with or without metal supports.

Figure 12:
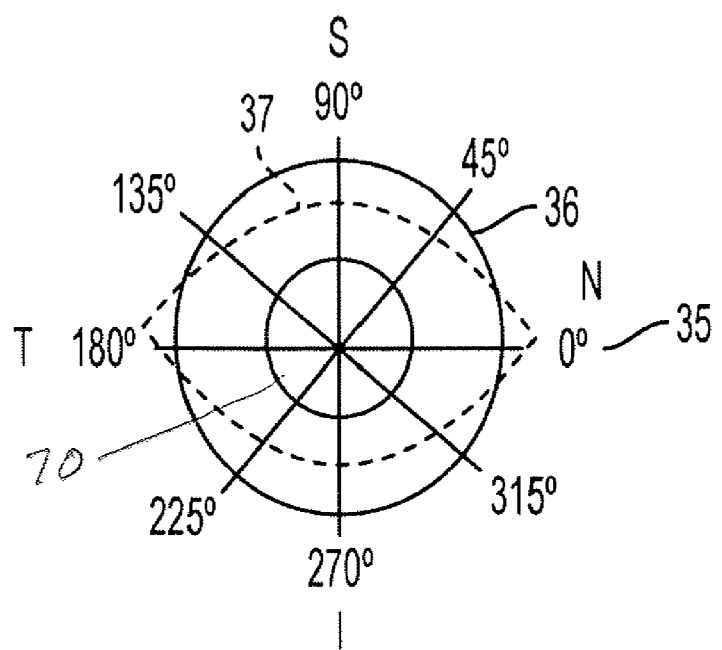
FIG. 12 shows the eye divided into compass degrees.
Figure 13A:
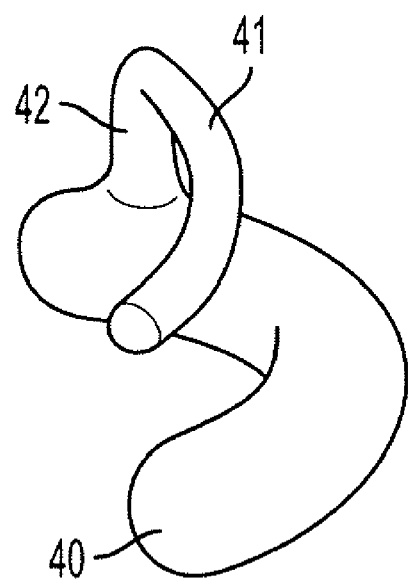
Figure 13C:
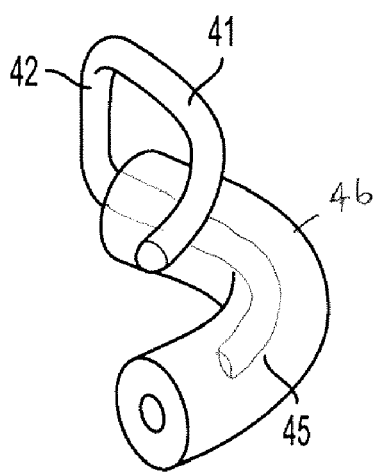
Figure 13D:
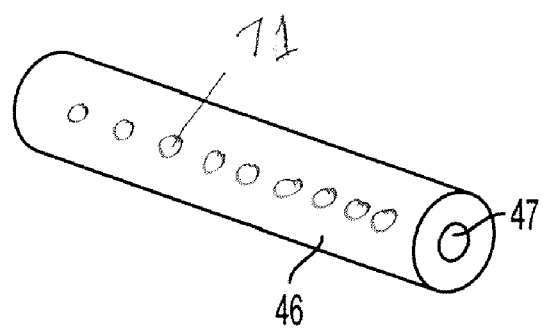

FIG. 12 depicts a diagram of a human eye from the physician's perspective. The eye (with the upper and lower lids in resting position) is noted by the dotted lines indicated by element 37. The actual globe, and physical portion of the eye subject to scleral depression, is represented by a continuous line circle indicated by element 36. The superior, nasal, inferior and temporal regions are indicated by the letters S, N, I and T, respectively. The circumferential angle for reference to scleral depression capability is noted by the angular measurements 35, which start with 0° at the nasal location. The cornea is represented by the circle 70 in the center of each eye diagram. The diagram show is for a right eye, the left eye being a mirror image. One of skill in the art will appreciate that scleral depressors of the present invention can be made to act on a portion of the eye from 1 degree to 360 degrees depending on the procedure. More than one depressor covering different areas may be used simultaneously or sequentially.

FIG. 13A-D depicts embodiments of a drug delivery concept for hands free scleral depression. In this example, a drug coating 40 may be place on the depressor element 44 directly. The drug may also be loaded into sleeves 46 which are placed over a depressor element 45. In some embodiments it may be desired to cover a coated depressor element 45 with a sleeve to delay or slow down the drug delivery or to provide additional quantities of drug or different drugs. In some embodiments the polymer sleeve may have several through holes 71 that allow for exposure of the drug to the fornix and/or more rapid elution of drug. Once exposed, the drug will elute through these holes directly into the fornix.

Drug eluting devices are known in the art and will be readily apparent to one of skill in the art. In one embodiment, provisions could be made for including a reservoir in the polymer sleeve 46. The pharmaceutical could be placed in the device prior to delivery, or inserted after the device has been placed. This polymer reservoir design could also provide the capability for a retinal surgeon to periodically place additional medicaments in the reservoir (of the same or different constituents) for the treatment of the retinal tissue bed. In the case of a drug eluting design, the device could be designed so as to direct drug elution into retinal tissue and prevent elution into the eye cavity. As shown in U.S. Pat. No. 6,720,402 the polymers can be designed to be collapsed at cooler temperatures and to unfold at body temperatures. The polymers could also be made from different layers, material durometers and may incorporate metallic or polymeric stiffening elements. There could also be a provision to allow for more than one device to be installed and as the patient improves, layers could be removed as desired until there were no layers left.

In yet another embodiment the implant further comprises a therapeutic drug. Such drug can be coated onto the depressor, or where the depressor is a polymer, incorporated into the structure via means known in the art, i.e., into an area with a surface treatment specifically intended to capture and release drug in a preferred manner or loaded into a reservoir incorporated into the device. Preferably, the device comprises biocompatible metals, metal alloys, biocompatible polymers or possibly combinations thereof. For example, a type of biocompatible polymer usable with the device according to the present invention includes the resilient polymeric materials disclosed in international publication WO 91/12779. Additional biocompatible metals and alloys include those disclosed, e.g., in U.S. Pat. Nos. 4,733,665; 4,800,882; 4,886,062; and 6,478,815, the contents of which are expressly incorporated herein by reference. Such metals and alloys include, but are not limited to, silver, tantalum, stainless steel, annealed steel, gold, copper alloys, cobalt alloys (e.g., cobalt-chromium-nickel alloys), titanium, tungsten, zirconium, niobium, iridium, and platinum. Shaped-memory metal alloys (e.g., Nitinol, a super elastic titanium alloy) can also be used to form the devices discussed herein.

Biocompatible polymers for use with the device of the present invention can be nonbioabsorbable, bioabsorbable in part, or substantially completely bioabsorbable. The stable, nonbioabsorbable polymers that may be used for device construction are those generally exhibiting a low chronic tissue response (including: irritation, adherence, inflammation. etc). These include polyesters, polyamides, polyolefins (substituted or unsubstituted with e.g., halides), polyurethanes (e.g., polyurethane urea, segmented polyurethane urea/heparin) and silicones (e.g., siliconeA, siliconeB, and silicone C)

In the event the device must be manufactured from a material which is not biocompatible, the use of biocompatible coatings can render the implant biocompatible. Biocompatible surfaces are important for medical devices. The term 'biocompatible' is used herein to mean a surface which causes either no or a minimal reaction when it comes into contact with a human or animal body or its blood, fluids or other biological membranes. Examples of biocompatible coatings are well known in the art and include, PTFE, hydroxyapatite and silicone. One of skill in the art will based on the materials in the implant know which coating are suitable. U.S. Pat. No. 6,406,792 teaches the use of coatings made by reacting a reactive polysiloxane. U.S. Pat. No. 3,574,673 teaches the use of organosiloxane polymers which can be cured on various surfaces such as needles to provide a lubricating film. Similarly, U.S. Pat. No. 4,720,521 teaches coating devices such as needles or catheters with a curable silicone composition to form a crosslinked, adherent coating which serves as a matrix for a non-reactive lubricating silicone polymer. U.S. Pat. No. 5,061,738 also teaches a blood compatible, lubricious composition for use on medical articles. The contents of the above patents are incorporated by reference, and are not considered limiting in choosing biocompatible coatings.

Polyesters include e.g., polyethylene terephthalate (PET) and polybutylene terephthalate (PBT). Other polyesters include polyethylene terephthalate copolymers or polybutylene terephthalate copolymers using, as comonomers, saturated dibasic acids such as phthalic acid, isophthalic acid, sebacic acid, adipic acid, azelaic acid, glutaric acid, succinic acid, and oxalic acid; polyethylene terephthalate copolymers or polybutylene terephthalate copolymers using, as diol comonomers, 1,4-cyclohexanedimethanol, diethylene glycol, and propylene glycol; and blends thereof. Specific examples of these polyethylene terephthalate copolymers include polyethylene terephthalate/isophthalate (PET/I), polyethylene terephthalate/sebacate (PET/S), and polyethylene terephthalate/adipate (PET/A). Specific examples of the polybutylene terephthalate polymers include polybutylene terephthalate (PBT), polybutylene terephthalate/isophthalate (PBT/I), polybutylene terephthalate/sebacate (PBT/S), polybutylene terephthalate/adipate (PBT/A), polybutylene/ethylene terephthalate, and polybutylene/ethylene terephthalate/isophthalate. Also usable are polyesters that are copolymerized or modified with other third components in order to improve their physical characteristics. The polyester resins may be stretched either monoaxially or biaxially.

Polyamides include, e.g., polyamides, Nylon 66, polycaprolactam, and molecules of the form $—NH—CH_2)_n—CO—$ and $NH—(CH_2)_x—NH—CO—(CH_2)_y—CO$, wherein n is preferably an integer in from about 6 to about 13, x is an integer from about 6 to about 12, and y is an integer from about 4 to about 16.

Polyolefins include, e.g., polypropylene, polyethylene, polyisobutylene, polytetrafluoroethylene, expanded polytetrafluoroethylene, ethylene-alphaolefin copolymers. Polyolefins also include copolymers of olefins and unsaturated glycidyl group-containing monomers, and terpolymers or multipolymers of olefins, unsaturated glycidyl group-containing monomers and ethylenically unsaturated monomers. Examples of olefins include propylene, butene-1, hexene-1, decene-1, octene-1. Examples of the unsaturated glycidyl group-containing monomers include e.g., glycidyl esters such as glycidyl acrylate, glycidyl methacrylate, monoglycidyl itaconate, monoglycidyl butenetricarboxylate, diglycidyl butenetricarboxylate, and triglycidyl butenetricarboxylate; glycidyl esters of .alpha.-chloroallyl, maleic acid, crotonic acid, and fumaric acid; glycidyl ethers such as vinyl glycidyl ether, allyl glycidyl ether, 2-methyallyl glycidyl ether, glycidyloxyethyl vinyl ether, and styrene-p-glycidyl ether; and p-glycidylstyrene. In addition to olefins, other ethylenically unsaturated monomers of the invention may also be used to form homo- or copolymers. Such monomers include, e.g., vinyl esters and .alpha.- and .beta.-ethylenically unsaturated carboxylic acids and derivatives thereof. Examples include vinyl esters such as vinyl acetate; vinyl propionate; vinyl benzoate; acrylic acid; methacrylic acid and esters thereof, such as methyl, ethyl, propyl, butyl, 2-ethylhexyl, cyclohexyl, dodecyl, and octadecyl acrylates or methacrylates; maleic acid; maleic anhydride; itaconic acid; fumaric acid; maleic mono and diesters; vinyl chloride; vinyl ethers such as vinyl methyl ether and vinyl ethyl ether; and acrylic amides.

Other useful nonbioabsorbable polymers include polyacrylamides, poly(meth)acrylates, polyalkyl oxides (polyethylene oxide), polyvinyl alcohol homo- and copolymers (e.g., PVA foams, polyethylene vinyl alcohol), polyethylene glycol homo- and copolymers, polylysine, polyoxamers, polysiloxanes (e.g., polydimethylsiloxane), polyethyloxazoline, and polyvinyl pyrrolidone, as well as hydrogels such as those formed from crosslinked polyvinyl pyrrolidinone and polyesters (e.g., polyvinyl pyrrolidone/cellulose esters and polyvinyl pyrrolidone/poly urethane) Further nonbioabsorbable polymeric materials include acrylic polymers (e.g., methacrylate) and copolymers, vinyl halide polymers and copolymers (e.g., polyvinyl chloride), polyvinyl ethers (e.g., polyvinyl methyl ether), polyvinylidene halides (e.g., polyvinylidene fluoride and polyvinylidene chloride), polymethylidene maleate, polyacrylonitrile, polyvinyl ketones, polyvinyl aromatics (e.g., polystyrene), polyvinyl esters (e.g., polyvinyl acetate), copolymers of vinyl monomers with each other and olefins (e.g., etheylene-methyl methacrylate copolymers, acrylonitrile-styrene copolymers, ABS resins and ethylene-vinyl acetate copolymers), alkyd resins, polycarbonates, polyoxymethylenes, polyimides, polyethers, epoxy resins, rayon, rayon-triacetate, cellulose, cellulose acetate, cellulose acetate butyrate, cellophane, cellulose nitrate, cellulose propionate, cellulose ethers (e.g., carboxymethyl cellulose and hydoxyalkyl celluloses), cellulose esters, and combinations thereof.

Preferred materials include those useful for manufacturing contact lenses including silicone elastomers, silicone-containing macromers including, without limitation, those disclosed in U.S. Pat. Nos. 5,371,147, 5,314,960, and 5,057,578 incorporated in their entireties herein by reference, hydrogels, silicone-containing hydrogels, and the like and combinations thereof. In some embodiments the lens material may contain a siloxane functionality, including, without limitation, polydimethyl siloxane macromers, methacryloxypropyl polyalkyl siloxanes, and mixtures thereof, a silicone hydrogel or a hydrogel, made of monomers containing hydroxy groups, carboxyl groups, or combinations thereof. Materials for making soft contact lenses are well known and commercially available and include acquafilcon, etafilcon, genfilcon, lenefilcon, balafilcon, lotrafilcon, or galyfilcon.

Bioabsorbable polymers may also be used for the manufacture of the present invention. Bioabsorbable polymers are advantageous in that the device or portions thereof formed from these materials can be absorbed into the body and therefore do not require physical removal. Bioabsorbable polymers include, for example, those found in Tanquay et al. (Contemp. Intervention. Tech. 12(4):699-713, (1994)). Bioabsorbable polymers differ from nonbioabsorbable polymers in that they can be degraded into substantially non-toxic biodegradation products, while used in in vivo therapy. Degradation generally involves breaking down the polymer into its monomeric subunits. For example, the ultimate hydrolytic breakdown products of a poly(phosphonate) are phosphonate, alcohol, and diol, all of which are potentially non-toxic. The rate of degradation of bioabsorbable polymers is related to various polymer properties, such as permeability, water solubility, crystallinity, and physical dimensions. In the contest of a bioabsorbable polymer the depressor could be designed to be left in place to deliver drug.

Bioabsorbable polymers include various types of aliphatic polyesters, polyorthoesters, polyphosphazenes, poly(amino acids), copoly(ether-esters), polyalkylene oxalates, polyamides, poly(iminocarbonates), polyoxaesters, polyamidoesters, polyoxaesters containing amido groups, poly(anhydrides), poly(hydroxybutyrates), polyphosphate-esters), polyurethanes, polyanhydrides, biomolecules, and blends thereof.

Bioabsorbable polyesters may be used and are described, e.g., in Pitt et al., "Biodegradable Drug Delivery Systems Based on Alipathic Polyesters: Application to Contraceptives and Narcotic Antagonists", Controlled Release of Bioactive Materials, 19-44 Richard Baker ed., (1980). Aliphatic polyesters include homopolymers and copolymers of lactides (including lactic acid and D-, L-, and meso lactide), .epsilon.-caprolactone, glycolide (including glycolic acid and lactide/glycolide copolymers), hydroxybutyrate, hydroxyvalerate, dioxanone (e.g., para-dioxanone), trimethylene carbonate (and its alkyl derivatives), 1,4-dioxepan-2-one, 1,5-dioxepan-2-one, 6,6-dimethyl-1,4-dioxan-2-one, and polymer blends thereof. Bioabsorbable polyorthoesters may also be used and are described e.g., by Heller et al., "Release of Norethindrone from Poly(ortho Esters)", Polymer Engineering Sci., 21:11, 727-31 (1981) and also by Heller in Handbook of Biodegradable Polymers, edited by Domb, Kost and Wisemen, Hardwood Academic Press (1997) p. 99-118. Polyorthoesters include, e.g., polyglycolic acid and polylactic acid such as poly-L-lactic acid (PLLA); poly D,L-lactic acid; and poly-D-lactic acid. Bioabsorbable polyphosphazenes are described, e.g., by Dunn et al., in U.S. Pat. Nos. 5,340,849; 5,324,519; 5,278,202; and 5,278,201. Polyphosphazenes, co-, ter- and higher order mixed monomer based polymers made from L-lactide, D,L-lactide, lactic acid, glycolide, glycolic acid, para-dioxanone, trimethylene carbonate and .epsilon.-caprolactone, are described by Allcock in The Encyclopedia of Polymer Science, Vol. 13, p. 31-41, Wiley Intersciences, John Wiley & Sons (1988) and by Vandorpe, Schacht, Dejardin and Lemmouchi in the Handbook of Biodegradable Polymers, edited by Domb, Kost and Wisemen, Hardwood Academic Press (1997), p. 161-182. Poly(amino acids) and pseudo-poly(amino acids) are described, e.g., by Pulapura et al., "Trends in the Development of Bioresorbable Polymers for Medical Applications," J. of Biomaterials Appl., 6:1, 216-50 (1992);

Poly(iminocarbonate) is described, e.g., in Kemnitzer and Kohn, Handbook of Biodegradable Polymers, edited by Domb, Kost and Wisemen, Hardwood Academic Press (1997), p. 251-272. Copoly(ether-esters) include, e.g., PEO/PLA and others described by Cohn and Younes, Journal of Biomaterials Research, Vol. 22 (1998), p. 993-1009, and by Cohn, Polymer Preprints (ACS Division of Polymer Chemistry) Vol. 30(1), (1989) p. 498. Polyalkylene oxalates include those described in U.S. Pat. Nos. 4,208,511; 4,141,087; 4,130,639; 4,140,678; 4,105,034; and 4,205,399. Polyanhydrides include those resulting from the polymerization of diacids of the form $HOOC-C_6H_4-O-(CH_2)_m-O-C_6H_4-COOH$ where m is an integer from about 2 to about 8 and also include copolymers resulting from the copolymerization of these diacids with aliphatic alpha-omega diacids of up to 12 carbons. As is known in the art, the monomer ratios in polyanhydride copolymers may be varied so that the resulting copolymer is surface eroding. Polyoxaesters, polyoxaamides, and polyoxaesters containing amines and/or amido groups are described in one or more of U.S. Pat. Nos. 5,464,929; 5,595,751; 5,597,579; 5,607,687; 5,618,552; 5,620,698; 5,645,850; 5,648,088; 5,698,213 and 5,700,583. Bioabsorbable polyphosphate-esters), e.g., poly(phosphates), poly(phosphonates) and poly(phosphites), are described, e.g., by Penczek et al., Handbook of Polymer Synthesis, Chapter 17: "Phosphorus-Containing Polymers", p. 1077-1132 (Hans R. Kricheldorf ed., 1992) and in U.S. Pat. No. 6,153,212. Bioabsorbable polyurethanes are described, e.g., by Bruin et al., "Biodegradable Lysine Diisocyanate-based Poly-(Glycolide-co-.epsilon.-Caprolactone)-Urethane Network in Artificial Skin", Biomaterials, 11:4, 291-95 (1990). Bioabsorbable polyanhydrides are described, e.g., by Leong et al., "Polyanhydrides for Controlled Release of Bioactive Agents", Biomaterials, 7:5, 364-71 (1986).

Polymeric biomolecules may also advantageously be used with the device or portions of the device according to the present invention. Polymeric biomolecules include naturally occurring materials that may be enzymatically degraded in the human body or those that are hydrolytically unstable in the human body. Such materials include albumin, alginate, gelatin, acacia, cellulose dextran, ficoll, hydroxyethyl cellulose, hydroxypropyl cellulose, hydroxypropylmethyl cellulose, carboxyethyl cellulose, carboxymethyl cellulose, fibrin, fibrinogen, collagen, elastin, dextran sulfate and absorbable biocompatible polysaccharides such as chitosan, deacetylated chitosan, starch, fatty acids (and esters thereof), glucoso-glycans and hyaluronic acid.

Other useful materials include bioabsorbable elastomers, preferably aliphatic polyester elastomers. In the proper proportions aliphatic polyester copolymers are elastomers. If used as coating materials, elastomers advantageously adhere well to the metal portions of the device and can withstand significant deformation without cracking Examples of suitable bioabsorbable elastomers are described in U.S. Pat. No. 5,468,253. Preferred bioabsorbable biocompatible elastomers are based on aliphatic polyesters, including elastomeric copolymers of ε.-caprolactone and glycolide (preferably having a mole ratio of ε-caprolactone to glycolide from about 35:65 to about 65:35); elastomeric copolymers of .epsilon.-caprolactone and lactide, including L-lactide, D-lactide and blends thereof or lactic acid copolymers (preferably having a mole ratio of .epsilon.-caprolactone to lactide from about 35:65 to about 90:10); elastomeric copolymers of p-dioxanone (1,4-dioxan-2-one) and lactide including L-lactide, D-lactide and lactic acid (preferably having a mole ratio of p-dioxanone to lactide from about 40:60 to about 60:40); elastomeric copolymers of .epsilon.-caprolactone and p-dioxanone (preferably having a mole ratio of .epsilon.-caprolactone to p-dioxanone from about 30:70 to about 70:30); elastomeric copolymers of p-dioxanone and trimethylene carbonate (preferably having a mole ratio of p-dioxanone to trimethylene carbonate from about 30:70 to about 70:30); elastomeric copolymers of trimethylene carbonate and glycolide (preferably having a mole ratio of trimethylene carbonate to glycolide from about 30:70 to about 70:30); elastomeric copolymers of trimethylene carbonate and lactide including L-lactide, D-lactide, and blends thereof; or lactic acid copolymers (preferably having a mole ratio of trimethylene carbonate to lactide from about 30:70 to about 70:30) and blends thereof.

The present invention also includes introducing an agent into a body using one of the above-discussed devices. In a preferred embodiment, the agent(s) is carried by one or more of the strands of the device and released within the body over a predetermined period of time. Local delivery of an agent is advantageous in that its effective local concentration is much higher when delivered by the device than that normally achieved by systemic administration. The device may carry one or more of the above-referenced agents for applying to a vessel as the vessel moves into contact with the agent carrying elements after deployment of the device within the eye. Drug delivery may also be achieved via other embodiments such as impregnated polymers, surface treatments of metals and polymers, polymers with reservoirs, etc.

The above-discussed device can deliver one or more known agents, including therapeutic and pharmaceutical agents, such as a drug, at a site of contact with a portion of the eye or when released from a carrier as is known. This release can be a timed release, release to a certain area of the retinal tissue bed, release generally to the eye or other arrangements as necessary. These agents can include any known therapeutic drugs, antiplatelet agents, anticoagulant agents, antimicrobial agents, antimetabolic agents and proteins used for the treatment, prevention, diagnosis, cure, or mitigation of disease or illness; substances that affect the structure of function of the body; and prodrugs, which become biologically active or more active after placement in a given physiological environment. Agents may include medicaments, vitamins, and mineral supplements. The agents may also include any of those disclosed in U.S. Pat. No. 6,153,252 to Hossainy et al. and U.S. Pat. No. 5,833,651 to Donovan et al., both of which are hereby incorporated by reference in their entirety.

Preferred agents usable with the implantable device disclosed herein are those that inhibit growth of tissue through any of a variety of approaches and include anti-inflammatory immuno-modulators including dexamethasone, m-prednisolone, interferon .gamma.-lb, leflunomide, sirolimus, everolimus, tacrolimus, mycophenolic acid, mizoribine, cyclosporine, rapamycin, and tranilast; antiproliferatives including QP-2, taxol, actinomycine, methotrexate, angiopeptin, vincristine, mitomycin, statins, CMYC antisense, ABT-578, RestenASE, 2-chlorodeoxyadenosine, PCNA ribozyme, paclitaxel, rapamycin, everolimus and tacrolimus; migration inhbitors/ECM-modulators including batimastat, prolylhydroxylase inhibitors, halofuginone, C-proteinase inhibitors, probucol, rapamycin, everolimus and tacrolimus; and agents that promote healing and reendothelialization including BCP671, VEGF, and estrogen. Additional agents, such as those discussed below, can also be used.

Non-limiting examples of agents include those within the following therapeutic categories: analgesics, such as non-steroidal anti-inflammatories (NSAIDs), steroidal anti-inflammatories, COX 2 selective inhibitors, opiate agonists and salicylates; angiogenesis inhibitors; antiasthmatics; antihistamines/antipruities, such as $H_1$-blockers and $H_2$-blockers; anti-infectives, such as anthelmintics, anti-anaerobics, antibiotics, aminoglycoside antibiotics, antifungal antibiotics, macrolide antibiotics, miscellaneous .beta.-lactam antibiotics, penicillin antibiotics, quinolone antibiotics, sulfonamide antibiotics, tetracycline antibiotics, antimicrobials, antibacterials, antimycobacterials, antituberculosis antimycobacterials, antiprotozoals, antimalarial antiprotozoals, antiviral agents, anti-retroviral agents, scabicides, and urinary anti-infectives; antiarthritics; antifibrinolytics; antineoplastics, such as alkylating agents, antimetabolites, purine analog antimetabolites, pyrimidine analog antimetabolites, hormonal antineoplastics, natural antineoplastics, antibiotic natural antineoplastics, and vinca alkaloid natural antineoplastics; calcium regulators; autonomic agents, such as anticholinergics, xanthines, mast cell stabilizers, antimuscarinic anticholinergics, ergot alkaloids, parasympathomimetics, cholinergic agonist parasympathomimetics, cholinesterase inhibitor parasympathomimetics, sympatholytics, .alpha.-blocker sympatholytics, .beta.-blocker sympatholytics, sympathomimetics, and adrenergic agonist sympathomimetics; cardiovascular agents, such as antianginals, .beta.-blocker antianginals, calcium-channel blocker antianginals, nitrate antianginals, antiarrhythmics, cardiac glycoside antiarrhythmics, class I, II, III, or IV antiarrhythmics, antihypertensive agents, .alpha.-blocker antihypertensives, angiotensin-converting enzyme inhibitor (ACE inhibitor) antihypertensives, .beta.-blocker antihypertensives, calcium-channel blocker antihypertensives, central-acting adrenergic antihypertensives, diuretic anti-hypertensive agents, peripheral vasodilator antihypertensives, anti-lipidemics, inotropes, cardiac glycoside inotropes, and thrombolytics/fibrinolytics; dermatological agents, such as antihistamines, anti-inflammatory agents, corticosteroid anti-inflammatory agents, and antipruritics/local anesthetics; electrolytic and renal agents, such as acidifying agents, alkalinizing agents, diuretics, carbonic anhydrase inhibitor diuretics, loop diuretics, osmotic diuretics, potassium-sparing diuretics, thiazide diuretics, electrolyte replacements, and uricosuric agents; enzymes, such as pancreatic enzymes and thrombolytic enzymes; gastrointestinal agents, such as anti-diarrheals, antiemetics/antinauseants, gastrointestinal anti-inflammatory agents, salicylate gastrointestinal anti-inflammatory agents, anti-ulcer/anti-reflux agents, antacid anti-ulcer agents, gastric acid-pump inhibitor anti-ulcer agents, gastric mucosal anti-ulcer agents, $H_2$-blocker anti-ulcer agents, cholelitholytic agents, digestants, emetics, laxatives and stool softeners, and prokinetic agents; enzyme inhibitors; general anesthetics, such as halogenated anesthetics, barbiturate anesthetics, benzodiazepine anesthetics, and opiate agonist anesthetics; hematological agents, such as antianemia agents, hematopoietic antianemia agents, coagulation agents, anticoagulants, hemorheologic agents, hemostatic coagulation agents, antiplatelet agents, thrombolytic enzyme coagulation agents, and plasma volume expanders; hormones, hormone modifiers, and thyroid hormones, such as abortifacients, adrenal agents, adrenal corticosteroids, androgens, anti-androgens, antidiabetics, sulfonylurea antidiabetic agents, antihypoglycemic agents, progestins, estrogens, fertility agents, oxytocics, parathyroid agents, pituitary hormones, antithyroid agents, thyroid hormones, and tocolytics; immunobiologic agents, such as immunoglobulins, immunosuppressives, toxoids, and vaccines; local anesthetics, such as amide local anesthetics and ester local anesthetics; musculoskeletal agents, such as anti-gout anti-inflammatory agents, corticosteroid anti-inflammatory agents, immunosuppressive anti-inflammatory agents, salicylate anti-inflammatory agents, skeletal muscle relaxants, neuromuscular blocker skeletal muscle relaxants, and reverse neuromuscular blocker skeletal muscle relaxants; anti-apoptotics; neurological agents, such as anticonvulsants, barbiturate anticonvulsants, benzodiazepine anticonvulsants, anti-migraine agents, anti-parkinsonian agents, anti-vertigo agents, opiate agonists, and opiate antagonists; ophthalmic agents, such as anti-glaucoma agents, .beta.-blocker anti-glaucoma agents, miotic anti-glaucoma agents, mydriatics, adrenergic agonist mydriatics, antimuscarinic mydriatics, ophthalmic anesthetics, ophthalmic anti-infectives, ophthalmic aminoglycoside anti-infectives, ophthalmic macrolide anti-infectives, ophthalmic quinolone anti-infectives, ophthalmic sulfonamide anti-infectives, ophthalmic tetracycline anti-infectives, ophthalmic agents, ophthalmic corticosteroid anti-inflammatory agents, and ophthalmic nonsteroidal anti-inflammatory drugs; psychotropic agents, such as antidepressants, heterocyclic antidepressants, monoamine oxidase inhibitors (MAOIs), selective serotonin re-uptake inhibitors (SSRIs), tricyclic antidepressants, antimanics, antipsychotics, phenothiazine antipsychotics, anxiolytics, sedatives, and hypnotics, barbiturate sedatives and hypnotics, benzodiazepine anxiolytics, sedatives, and hypnotics, and psychostimulants; respiratory agents, such as antitussives, bronchodilators, adrenergic agonist bronchodilators, antimuscarinic bronchodilators, expectorants, mucolytic agents, respiratory anti-inflammatory agents, and respiratory corticosteroid anti-inflammatory agents; toxicology agents, such as antidotes, heavy metal antagonists/chelating agents, substance abuse agents, deterrent substance abuse agents, and withdrawal substance abuse agents; minerals; vitamins, such as vitamin A, vitamin B, vitamin C, vitamin D, vitamin E, and vitamin K; amino acids; and proteins, such as antibodies (e.g., monoclonal antibodies, polyclonal antibodies, and antibody fragments).

The following are examples of agents within the various therapeutic categories discussed above that can be used alone or with another one or more of these agents or specifically formulated to deliver optimal therapeutic effect in one or more of the device embodiments:

Analgesics include, e.g., para-aminophenol derivatives (e.g., acetaminophen), indole and indene acetic acids (e.g., etodalac), heteroaryl acetic acids (e.g., diclofenac and ketorolac), arylpropionic acids (e.g., ibuprofen), anthranilic acids (e.g., mefenamic acid and meclofenamic acid), enolic acids (e.g., tenoxicam and oxyphenthatrazone), nabumetone, gold compounds (e.g., gold sodium thiomalate), buprenorphine, propoxyphene hydrochloride, propoxyphene napsylate, meperidine hydrochloride, hydromorphone hydrochloride, morphine, oxycodone, codeine, dihydrocodeine bitartrate, pentazocine, hydrocodone bitartrate, levorphanol, diflunisal, trolamine salicylate, nalbuphine hydrochloride, mefenamic acid, butorphanol, choline salicylate, butalbital, phenyltoloxamine citrate, methotrimeprazine, cinnamedrine hydrochloride, meprobamate, ketoprofen, flurbiprofen, naproxen, ramifenazone, meloxicam, fluazacort, celecoxib, rofecoxib, valdecoxib, nepafenac, ISV-205; angiogenesis inhibitors include, e.g., angiostatin (plasminogen fragment), vascular endothelial cell growth factor (VEGF), fibroblast growth factor (FGF), nitric oxide donors, antiangiogenic anithrombin III, cartilage-derived inhibitor (CD1), CD59 complement fragment, endostatin (collagen XVIII fragment), fibronectin fragment, gro-beta, heparinases, heparin hexasaccharide fragment, human chorionic gonadotropin (hCG), .alpha.-, .beta.-, and .gamma.-interferon, interferon inducible protein (IP-10), interleukin-12, kringle 5 (plasminogen fragment), metalloproteinase inhibitors (TIMPs), 2-methoxyestradiol, placental ribonuclease inhibitor, plasminogen activator inhibitor, platelet factor-4 (PF-4), prolactin 16 kD fragment, proliferin-related protein (PRP), retinoids, tetrahydrocortisol-S, thrombospondin-1 (TSP-1), transforming growth factor-beta (TGF-b), vasculostatin, vasostatin (calreticulin fragment), apolipoprotein E, TBC-2576; antiasthmatics include, e.g., ketotifen and traxanox; antidepressants include, e.g., nefopam, oxypertine, amoxapine, trazodone, maprotiline, phenelzine, desipramine, nortriptyline, tranylcypromine, fluoxetine, doxepin, imipramine, imipramine pamoate, isocarboxazid, trimipramine, and protriptyline; antidiabetics include, e.g., biguanides (e.g., metformin), sulfonylurea derivatives (e.g., tolbutamide, chlorpropamide, acetohexamide, tolazamide, and glimepiride), .alpha.-glucosidase inhibitors (e.g., acarbose), thiazolidinediones (e.g., troglitazone), and metglinide analogs (e.g., repaglinide); antihypertensive agents include, e.g., propanolol, propafenone, oxyprenolol, reserpine, trimethaphan, phenoxybenzamine, pargyline hydrochloride, deserpidine, diazoxide, guanethidine monosulfate, minoxidil, rescinnamine, sodium nitroprusside, rauwolfia serpentina, alseroxylon, and phentolamine; antineoplastics include, e.g., cladribine (2-chlorodeoxyadenosine), nitrogen mustards (e.g., cyclophosphamide, mechlorethamine, melphalan, and chlorambucil), ethylenimines and methylmelamines (e.g., hexamethylmelamine and thiotepa), alkyl sulfonates (e.g., busulfan), nitrosoureas (e.g., streptozocin, carmustine (BCNU), methyl-CCNU and analogs), trazenes (e.g., dacarbazinine (DTIC)), platinum coordination complexes (e.g., carboplatin and cisplatin), procarbazine, hydroxyurea, mitotane, aminoglutethimide, camptothecin phenesterine, paclitaxel, docetaxel, vinca alkaloids (e.g., vinblastine, vincristine, and vinorelbine), epidipodophyllotoxins (e.g., etoposide (VP-16) and teniposide), tamoxifen, and piposulfan; anxiolytics include, e.g., lorazepam, buspirone, prazepam, chlordiazepoxide, oxazepam, clorazepate dipotassium, hydroxyzine pamoate, hydroxyzine hydrochloride, alprazolam, droperidol, halazepam, chlormezanone, and dantrolene; enzyme inhibitors include, e.g., selegiline or its hydrochloride salt, lazabemide, rasagiline, moclobemide, entacapone, tolcapone, nitecapone, Ro 40-7592, clozapine, risperidone, olanzapine, and quetiapine; immunosuppressives include, e.g., calcineurin inhibitors (e.g., cyclosporine and tacrolimus (FK-506)), antiproliferative/antimetabolic agents (e.g., sirolimus, QP-2, taxol, actinomycin, dactinomycin, daunorubicin, angiopeptin, mitomycine, bleomycin, doxorubicin, epirubicin, mitomycin, idarubicin, anthracyclines, mitoxantrone, plicamycin, CMYC antisense, ABT-578, RestenASE, 2-chloro deoxyadenosine, PCNA ribozyme, rapamycin, folic acid analogs (e.g., methotrexate), fluorouracil (5-FU), floxuridine, cytarabine, mercaptopurine, thioguanine, pentostatin, cyclophosphamide, thalidomide, chorambucil, leflunomide, batimastat, and mizoribine), everolimus, azathioprine, cytoxan, mycophenolic acid, mycophenolate mofetil, and tranilast; antimigraine agents include, e.g., ergotamine, isometheptene mucate, and dichloralphenazone; sedatives and hypnotics include, e.g., barbiturates (e.g., pentobarbital and secobarbital), flurazepam hydrochloride, triazolam, and midazolam; calcium-channel blocker antianginals include, e.g., nifedipine and diltiazem; nitrate antianginals include, e.g., nitroglycerin, isosorbide dinitrate, pentaerythritol tetranitrate, and erythrityl tetranitrate; antipsychotics include, e.g., haloperidol, loxapine succinate, loxapine hydrochloride, thioridazine, thioridazine hydrochloride, thiothixene, fluphenazine, fluphenazine decanoate, fluphenazine enanthate, trifluoperazine, chlorpromazine, perphenazine, lithium citrate, and prochlorperazine; antimanics include, e.g., lithium carbonate; antiarrhythmics include, e.g., bretylium tosylate, esmolol, verapamil, amiodarone, encainide, digoxin, digitoxin, mexiletine, disopyramide phosphate, procainamide, quinidine sulfate, quinidine gluconate, quinidine polygalacturonate, flecainide acetate, tocainide, and lidocaine; antiarthritics include, e.g., phenylbutazone, sulindac, penicillanine, salsalate, piroxicam, indomethacin, meclofenamate, ketoprofen, auranofin, aurothioglucose, tolmetin, and tolmetin sodium; anti-gout agents include, e.g., colchicine and allopurinol; anticoagulants include e.g., danaparoid, lepirudin, dicumarol, acenocoumarol, heparin, heparin salts (e.g., heparin sodium), warfarin sodium, 4-hydroxycoumarin, phenprocoumon, indan-1,3 dione, anisindione, warfarin sodium, tissue factor pathway inhibitor (TFPI), tifacogin, ancrod, bromindione, clorindione, coumetarol, cyclocoumarol, 4-coumarinol, desirudin, dexran sodium sulfate, diphenadione, ethyl biscoumacetate, fluindione, hirudin, nadroparin calcium, nafamostat mesylate, oxazidione, phenindione, phosvitin, picotamide, sodium apolate, thrombocid, tioclomarol, warfarin, aprosulate sodium, ART 123, bivalirudin, BMS 189090, BMS 186282, BMS 189664, BMS 191032, corsevin M, CS 747, curdlan sulfate, DPC 423, DX 9065a, efegatran, fondaparinux sodium, GR 144053, inogatran, LB 30057, melagatran, MR 33, napsagatran, NSL 9403, SR 90107, YM 75466, ZK 805412, ZK 807834, OGS 15435, JTV 803, LY 287045, P 8720, RE 1492, Ro 43-8857, S 18326, S 31214, SK 549, SB 249417, SR 123781A, and UK 156406; thrombolytics/fibrinolytics include, e.g., urokinase, streptokinase, alteplase, phosphorylcholine, plasmin, plasminogen, angiokinase, anistreplase, prourokinase, reteplase, saruplase, tissue plasminogen activator, actinokinase, .alpha.2-antiplasmin, antithrombin, E 6010, fibrolase, lys-plasminogen, lanoteplase, lumbrokinase, metalloproteinase, monteplase, PAI proteinase inhibitor, pamiteplase, staphylokinase, and tenecteplase; antifibrinolytics include, e.g., aminocaproic acid; hemorheologic agents include, e.g., pentoxifylline; antiplatelet agents include, e.g., aspirin, ticlopidine, abciximab, clopidogrel, eptifibatide, tirofiban, and glycoprotein IIb/IIa inhibitors, argatroban, cilostazole, cloricromene, dalteparin, daltroban, defibrotide, dipyridamole, enoxaparin, iloprost, indobufen, isbogrel, lamifiban, lotrifiban nadroparin calcium, orbofiban, pamicogrel KBT 3022, plafibride, picotamide, ozagrel, ramatroban, reviparin sodium, ridogrel, roxifiban, satigrel, sibrafiban, sulotroban, taprostene, ticlopidine, triflusal, amrinone, cilostamide, dialzep, enoximone, milrinone, naftazone, pimilprost, pimobendan, sarpogrelate, sulfinpyrazone, vapiprost, vesnarinone, xemilofiban, zaprinast, zeria Z 335, A 02131-1, camonagrel, cangrelor, DMP 728, DMP 802, elarofiban, EMD 122347 FK 633, FXV 673, ifetroban, L 734217, lefradafiban, MK 852, ON 579, R 99224, RGD 039, RGD 891, RPR 109891, Ro 48-3657, Ro 44-3888, S 1197, SDZ-GPI 562, SL 650472, SM 20302, SR 121566A, SR 121787A, TA 993, TAK 029, XV 454, XV 459, YC-1, aspalatone, BAY 41-2272, BM 531, BM 14515, C 186-65, CS 570, FR 158999, fradafiban, L 750034, linotroban, ME 3277, MED 27, NQ 12, NQ 301, NQ 304, NSL 9511, NSP 513, 4-pentynoic acid, 3-[[4-[[4-(aminomethyl)-phenyl] amino-]-1,4-dioxobutyl]-amino]-ethyl ester, RE 2047, SCH 79797, SM 10906, SR 25989, TP 9201, XJ 735, XR 300, XU 057, XU 063, XU 065, Y 909, ZD 2486, and ZD 9583; anti-apoptotics include, e.g., CGP 3466, CEP-1347/KT-7515, TCH-346, and WHI-P131; neurological agents include, e.g., timolol, dapiprazole, levobunolol, betaxolol, befunolol, carteolol, metipranolol, AMO-140, bunazosin, adaprolol, ISV-208, L-653328, cetamolol, H-216/44, KRG-332, levobetaxolol, metazosin, NCX-904, NCX-905, guanethidine, brimonidine, apraclonidine, AGN-195795, AGN-191103, AGN-190532, AGN-192172, AGN-193080, AGN-190837, talipexole, thiourea, dipivefrin, epinephrine, phenylephrine, cocaine, hydroxyamphetamine, naphazoline, tetrahydrozoline, levodopa, levodopa/carbidopa, levodopa/benserazide, amantadine, sumanirole, pergolide, pramipexole, ropinirole, bromocriptine, lisuride or 9, 10 dihydrolisuride, apomorphine or N-propylnoraporphine, N-propyl noraporphine, PHNO, N-0437 (racemate) and N-9023 (purified negative enantiomer), cabergoline, ciladopa, ABT-431, lergotrile, DIB1508Y, and ABT418m; selective serotonin re-uptake inhibitors (SSRIs) include, e.g., paroxetine, and serataline; anticonvulsants include, e.g., valproic acid, divalproex sodium, phenytoin, phenytoin sodium, clonazepam, primidone, phenobarbitol, carbamazepine, amobarbital sodium, methsuximide, metharbital, mephobarbital, mephenytoin, phensuximide, paramethadione, ethotoin, phenacemide, secobarbitol sodium, clorazepate dipotassium, and trimethadione; anti-parkinsonian agents include, e.g., ethosuximide; antihistamines/antipruritics include, e.g., hydroxyzine, chlorpheniramine, brompheniramine maleate, cyproheptadine hydrochloride, terfenadine, clemastine fumarate, triprolidine, carbinoxamine, diphenylpyraline, phenindamine, azatadine, tripelennamine, dexchlorpheniramine maleate, and methdilazine; calcium regulators include, e.g., calcitonin and parathyroid hormone; antibacterials include, e.g., amikacin sulfate, aztreonam, chloramphenicol, chloramphenicol palirtate, clindamycin, clindamycin palmitate, clindamycin phosphate, metronidazole, gentamicin sulfate, lincomycin hydrochloride, tobramycin sulfate, vancomycin hydrochloride, polymyxin B sulfate, colistimethate sodium, and colistin sulfate; antibiotics include, e.g., neomycin, streptomycin, chloramphenicol, cephalosporin, ampicillin, penicillin, tetracycline, and ciprofloxacin; antifungal antibiotics include, e.g., griseofulvin, ketoconazole, itraconizole, amphotericin B, nystatin, and candicidin; antiviral agents include, e.g., zidovudine (AZT), amantadine hydrochloride, ribavirin, and acyclovir; antimicrobials include, e.g., cephalosporins (e.g., cefazolin sodium, cephradine, cefaclor, cephapirin sodium, ceftizoxime sodium, cefoperazone sodium, cefotetan disodium, cefuroxime e azotil, cefotaxime sodium, cefadroxil monohydrate, cephalexin, cephalothin sodium, cephalexin hydrochloride monohydrate, cefamandole nafate, cefoxitin sodium, cefonicid sodium, ceforanide, ceftriaxone sodium, cefadroxil, and cefuroxime sodium), penicillins (e.g., ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G procaine, methicillin sodium, and nafcillin sodium), and erythromycins (e.g., erythromycin ethylsuccinate, erythromycin, erythromycin estolate, erythromycin lactobionate, erythromycin stearate, and erythromycin ethylsuccinate), and tetracyclines (e.g., tetracycline hydrochloride, doxycycline hyclate, minocycline hydrochloride, azithromycin, and clarithromycin); anti-infectives include, e.g., GM-CSF; sympathomimetics include, e.g., epinephrine hydrochloride, metaproterenol sulfate, terbutaline sulfate, isoetharine, isoetharine mesylate, isoetharine hydrochloride, albuterol sulfate, albuterol, bitolterolmesylate, isoproterenol hydrochloride, epinephrine, and epinephrine bitartrate;

anticholinergics include, e.g., ipratropium bromide, benzhexol, trihexphenidyl, benzotropine, diphenhydramine hydrochloride, orphenadrine, chlorphenoxamine, amitriptyline, doxepin, imipramine, nortriptyline, biperiden, ethopropazine, procyclidine, cycrimine, and ethopropzaine; xanthines include, e.g., aminophylline, dyphylline, metaproterenol sulfate, and aminophylline; mast cell stabilizers include, e.g., cromolyn sodium; bronchodilators include, e.g., salbutamol, budesonide, ketifen, salmeterol, xinafoate, terbutaline sulfate, theophylline, nedocromil sodium, metaproterenol sulfate, flunisolide, and fluticasone proprionate; androgens include, e.g., danazol, testosterone cypionate, fluoxymesterone, ethyltestosterone, testosterone enathate, methyltestosterone; estrogens include, e.g., estradiol, estropipate, and conjugated estrogens; progestins include, e.g., methoxyprogesterone acetate, and norethindrone acetate; adrenal corticosteroids include, e.g., cortisol, cortisone, oxandrolone, creatine, erythropeotin, dehydroepiandrosterone triamcinolone, betamethasone, betamethasone sodium phosphate, dexamethasone, dexamethasone sodium phosphate, dexamethasone acetate, prednisone, prednisolone, methylprednisolone acetate suspension, triamcinolone acetonide, hydrocortisone sodium succinate, triamcinolone hexacetonide, hydrocortisone, hydrocortisone cypionate, fludrocortisone acetate, paramethasone acetate, prednisolone tebutate, and prednisolone acetate; thyroid hormones include, e.g., levothyroxine sodium; antihypoglycemic agents include, e.g., human insulin, purified beef insulin, purified pork insulin, glyburide, chlorpropamide, glipizide, tolbutamide, and tolazamide; anti-lipidemics include e.g., antiatheroscleotics and antihypercholesteremics (e.g., cholesteryl ester transfer protein (CETP) inhibitors, such as those disclosed in U.S. Pat. No. 6,458,850; ileal bile acid transport (IBAT) inhibitors, such as those disclosed in U.S. Pat. No. 6,458,851; and HMG CoA reductase inhibitors, such as those disclosed in U.S. Pat. No. 6,462,091), fibric acid derivatives (e.g., clofibrate, fenofibrate, ciprofibrate, benzafibrate, clinofibrate, binifibrate and gemfibrozil), and nicotinic acid derivatives (e.g., nicotinic acid, niceritrol, and acipimox), dextrothyroxine sodium, probucol, pravastatin, atorvastatin, lovastatin, and niacin; antiulcer/antireflux agents include, e.g., famotidine, cimetidine, and ranitidine hydrochloride; antiemetics/antinauseants include, e.g., meclizine hydrochloride, nabilone, prochlorperazine, dimenhydrinate, promethazine hydrochloride, thiethylperazine, and scopolamine; collagen synthesis inhibitors include, e.g., prolyl hydroxylase inhibitors, C-proteinase inhibitors, and halofuginone; vitamins include oil-soluble vitamins (e.g., vitamins A, D, E, and K); amino acids include, e.g., valine, leucine, and isoleucine; proteins include, e.g., cyclophilin, antithymocyte globulin, immunoglobulin, muromonab-CD3, daclizumab, basiliximab, infliximab, etanercept, DNase, alginase, L-asparaginase, superoxide dismutase (SOD), lipase, metallothionine, a polipoprotein E, oxandrolone, creatine, dehydro epiandrosterone, platelet derived growth factor, fibrin, fibrinogen, collagen, interleukins 1 through 18, luteinizing hormone releasing hormone (LHRH), gonadotropin releasing hormone (GnRH), and transforming growth factor-.beta. (TGF-.beta.), tumor necrosis factor-.alpha. and .beta. (TNF-.alpha. and .beta.), nerve growth factor (NGF), growth hormone releasing factor (GHRF), epidermal growth factor (EGF), fibroblast growth factor homologous factor (FGFHF); hepatocyte growth factor (HGF); insulin growth factor (IGF), invasion inhibiting factor-2 (IIF-2), bone morphogenetic proteins 1-7 (BMP 1-7), somatostatin; thymosin-.alpha.-1, and .gamma.-globulin. Various biologically active forms of these proteins, including recombinant forms, mutants, complements, analogs, derivatives, and fragments are also contemplated. Other useful agents include nucleic acids (e.g., sense or anti-sense nucleic acids encoding any therapeutically useful protein, including any of the proteins described herein).

A description of other categories of useful agents and other individual agents can be found in Martindale, The Extra Pharmacopoeia, 30.sup.th Ed. (The Pharmaceutical Press, London 1993).

Examples of other agents that may be delivered using the device of the present invention include chlorhexidine, estradiol cypionate, estradiol valerate, flurbiprofen sodium, ivermectin, nafarelin, beta-glucan, bovine immunoglobulin, bovine superoxide dismutase, HIV-1 immunogen, human anti-TAC antibody, CD34 antibody, recombinant human growth hormone (r-hGH), recombinant human hemoglobin (r-Hb), recombinant human mecasermin (r-IGF-1), lenograstim (G-CSF), recombinant thyroid stimulating hormone (r-TSH), topotecan, aldesleukin, atenolol, epoetin alfa, leuprolide acetate, ceftriaxone, ceftazidime, oxaprozin, breveldin, valacyclovir, urofollitropin, famciclovir, flutamide, enalapril, mefformin, itraconazole, gabapentin, fosinopril, tramadol, lorazepan, follitropin, omeprazole, fluoxetine, lisinopril, tramsdol, levofloxacin, zafirlukast, growth hormone, granulocyte stimulating factor, nizatidine, bupropion, perindopril, erbumine, adenosine, alendronate, alprostadil, benazepril, bleomycin sulfate, dexfenfluramine, fentanyl, flecainid, gemcitabine, glatiramer acetate, granisetron, lamivudine, mangafodipir trisodium, mesalamine, metoprolol fumarate, miglitol, moexipril, monteleukast, octreotide acetate, olopatadine, paricalcitol, somatropin, sumatriptan succinate, tacrine, trovafloxacin, dolasetron, finasteride, isradipine, lansoprazole, terbinafine, pamidronate, didanosine, cisapride, venlafaxine, fluvastatin, losartan, imiglucerase, donepezil, valsartan, fexofenadine, BCP 671, adapalene, doxazosin mesylate, mometasone furoate, ursodiol, enalapril maleate, felodipine, nefazodone hydrochloride, valrubicin, albendazole, conjugated estrogens, medroxyprogesterone acetate, nicardipine hydrochloride, zolpidem tartrate, amlodipine besylate, ethinyl estradiol, rubitecan, amlodipine besylate/benazepril hydrochloride, etodolac, paroxetine hydrochloride, atovaquone, podofilox, betamethasone dipropionate, pramipexole dihydrochloride, Vitamin D3 and related analogs, quetiapine fumarate, candesartan, cilexetil, fluconazole, ritonavir, flumazenil, carbemazepine, carbidopa, ganciclovir, saquinavir, amprenavir, sertraline hydrochloride, carvedilol, halobetasolproprionate, sildenafil citrate, chlorthalidone, imiquimod, simvastatin, citalopram, irinotecan hydrochloride, sparfloxacin, efavirenz, cisapride monohydrate, tamsulosin hydrochloride, mofafinil, letrozole, terbinafine hydrochloride, rosiglitazone maleate, diclofenac sodium, lomefloxacin hydrochloride, tirofiban hydrochloride, telmisartan, diazapam, loratadine, toremifene citrate, dinoprostone, mefloquine hydrochloride, trandolapril, tretinoin, nelfinavir mesylate, indinavir, beclomethasone dipropionate, isotretinoin, tamoxifen citrate, nimodipine, latanoprost, travoprost, unoprostone, AL-10682, AL-3138, AGN-191976, PhXA-34, AL-16082, bimatoprost, ethanolamide, dorzolamide, brinzolamide, acetazolamide, methazolamide, L-662583, MK-927, L-693612, L-685393, mannitol, glycerol, isosorbide, physostigamine, echothiophate, acetylcholine, methacholine, pilocarpine, aceclidine, carbachol, demecarium, isofluorphate, memantine, iomerizine, H-7, SR-43845, enalkiren, Y-39983, GPI-5693, anadamide, L-768242, L-759787, dexanabinol, collagenase ABC, iomefloxacin, iosartan, CS-088, mecobalamin, ISV-900, cardiotrophin-1, S-1033, D-22A, pentigetide, lerdelimumab, DE-085, SR-121463, org-34517, octamer, NNC-26-9100, KSR-592, A-75169, ethacrynate sodium, SDZ-GLC-756, rostaporfin, proxodolol, WIN-552122, OSA-8302, AL-16049, naboctate, L-696986, AL-4333A, vaninolol, PCA-50941, HGP-32, AGN-192836, AGN-191970, WP-934, ACC-9002, AL-4623A, L-4414A, CK-119, alprenoxime, CBT-101, AGN-191151, H 21644, SL 1111, GPI-5232, eliprodil, tilisolol, lomerizine, riluzole, lamotrigine, dextromethorphan, EAAT2, topiramate, AP5, CPP, selfotel or CGS 19755, CGP 37849, CGP 39551, CGP 40116, NPC 17742, aptiganel/ CNS 1102, dextromethorphan and enzyme inhibitor, FR 115427, ketamine, ketobemidone, methadone, dizocilpine or MK 801, PCP, pethidine, RPR-1 19990, LY-300164 or talampanel, CNQX, DNQX, LY 215490, NNC 079202 or NBQX, NS 257, GYKI 52466, cyclothiazide, IDRA 21, DCG-IV, glycine, AP4, t-ACPD, L-SOP, L-AP3, S-4C3HPG, S-4CPG, MAP-4, RS-M4CPG, N-(3-[5-chloro-1-(4-chlorophenyl[indan-1-yl]propyl)-N-methylalanine, SR-57746A, T-588, 3,4 diaminopyridine, CPC-304, CPC-317, PD-176078, cephalosporin ceftriaxone, huperzine A, 10-methylhuperzine A, 10,10 dimethyl huperzine A, huperzine B, nicotine, epibaticline, cytosine, lobeline, anabasine, CNTF, BNDF, rhIGF-1, myotrophin mecasermin, Somatomedin C, GDNF, liatermin, neurturin, PEDF, FKBO-neuro-immunophilin ligands, AIT-082, leteprinim potassium, neotrofinT, emfilermin, CT-1, NT-3, NT-4/5, EHT 201, EHT 202, genistein, RX-77368, MK-771, JTP-2942, GPI-5000, ZVAD fink, 3-(2-phenyl-2-oxoethyl)-4,5-dimethylthiazolium salt, nordihydroguaiaretic acid, L-655238, Bay-X-1005, ML-3000, zileuton, oxothiazolidine carboxylate, ARR 17477, SOD, recombinant human CuZn-SOD, glutathione, glutathione peroxidase, catalase, nitric oxide synthase, vitamin E, vitamin C, selenium, acetylcysteine, seleginine, pycnogenol, co-enzyme Q10, beta carotene, PC 01, SC-55858, edaravone, iron (III) porphyrins, chromomycin, daunomycin, olivomycin, WP-631, DHEA, baclofen, tizandidine, dronabinol, diazepam, AVP-923, amitriptylene, fluvoxamine, sertraline, glycopyrrolate, copolamine, trihexyphenidyl, clonidine, propantheline, tropine, docusate sodium, tolterodine, TA-0910, ubiquinone, alpha lipoic acid, NAC, polyphenols, pregnenolone, threonine, methylcobalamin, metaxalone, tizanadine, carisoprodol, cyclobenzaprine, tramadol, potassium, calcium, zinc, magnesium, botulinum neurotoxin, succinylcholine, decamethonium, quinine, tetrahydrocannabinol, d-tubocurarine, atracurium, doxacurium, mivacurium, cistracurium besilate, pancuronium, pipecuronium bromide, rapacuronium bromide, rocuronium, vecuronium bromide, atracurium, suxamethonium; alcuronium, curare, metocurine, gallamine, nitrazepam, nordazepam, vigabatrin, procaine, chloroquine, gluthathione, odansetron, memantadine, GPI-1046, eradoline U-69 593, KW 6002, remacemide, dextromethorphan, NS-2214, CD133 antigen, CD34 antigen and reboxetine.

In addition to the above agents, there are a number of viruses, live or inactivate, including recombinant viruses that may, with the device of the present invention, be used to deliver nucleic acids to the vessel walls of a lumen. Treatment involves either the expression of a gene to provide a therapeutic effect to a cell or the expression of a gene to i) replace a mutated gene in a cell, ii) augment expression of a protein in a cell, or iii) inhibit a gene in a cell.

Of the therapeutic categories specified above, one set of preferred categories are those associated with treating disorders of the eye that may or are likely to require the use of the present invention. Other preferred categories are those associated with the prevention or treatment of side effects (e.g., infection) possibly accompanying device insertion. Preferred therapeutic categories include hematological agents, preferably antiplatelet agents and anticoagulants; anti-infectives, preferably antimicrobials, antibacterials, antiviral agents, and antibiotics; immunobiologic agents, preferably immunosuppressives; proteins, preferably antibodies; cardiovascular agents, preferably anti-lipidemics, and thrombolytics/fibrinolytics; angiogenesis inhibitors; anti-apoptotics; antineoplastics; and collagen synthesis inhibitors.

The above agents may be used in any known pharmaceutically acceptable form. The term "pharmaceutically acceptable" refers to the agents being appropriate for use in vivo. For example, pharmaceutically acceptable forms include various metallic ion and organic ion forms. Metallic ions include, but are not limited to, alkali metal ions, alkaline earth metal ions and other physiological acceptable metal ions. Exemplary ions include aluminum, calcium, lithium, magnesium, potassium, sodium and zinc ion forms, where the ions are in their usual valences. Preferred organic ions include protonated tertiary amines and quatenary ammonium cations, including in part, trimethylamine, diethylamine, N,N'-dibenzylethylenediamine, chloroprocaine, choline, diethanolamine, ethylenediamine, meglumine (N-methylglucamine) and procaine.

Also included as pharmaceutically acceptable forms are various acid forms of the above agents. Exemplary pharmaceutically acceptable acids include, without limitation, hydrochloric acid, hydroiodic acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid oxalacetic acid, fumaric acid, propionic acid, aspartic acid, glutamic acid, and benzoic acid. Further pharmaceutically acceptable forms include various salt forms of the above agents. Illustrative pharmaceutically acceptable salts are prepared from formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, stearic, salicylic, p-hydroxybenzoic, phenylacetic, mandelic, embonic (pamoic), methanesulfonic, ethanesulfonic, benzenesulfonic, pantothenic, toluenesulfonic, 2-hydroxyethanesulfonic, sulfanilic, cyclohexylaminosulfonic, algenic, .beta.-hydroxybutyric, galactaric and galacturonic acids.

Other pharmaceutically acceptable salt forms are the base addition salt forms of the agents described above. Illustrative pharmaceutically acceptable base addition salts include metallic ion salts and organic ion salts. Preferred metallic ion salts include appropriate alkali metal (group Ia) salts, alkaline earth metal (group IIa) salts and other known physiological acceptable metal ions. Such salts can be made from the ions of aluminum, calcium, lithium, magnesium, potassium, sodium and zinc. Preferred organic salts can be made from tertiary amines and quaternary ammonium salts, including in part, trimethylamine, diethylamine, N,N'-dibenzylethylenediamine, chloroprocaine, choline, diethanolamine, ethylenediamine, meglumine (N-methylglucamine) and procaine.

Also, other pharmaceutically acceptable forms of the above agents include the various isomeric forms (e.g., purified structural isomers; purified stereoisomers such as diastereomers and enantiomers; and purified racemates), tautomers, esters, amides and prodrugs of these agents.

Any one or more of the above-discussed agents may be coated onto the device or parts thereof parts of the device, in any conventional manner, such by a spray coating, vapor deposition, simple dip coating or, if a thicker coating of the therapeutic agent is desired, multiple dip coatings of the same or multiple agents. The agents may be applied directly onto the device in multiple layers. Methods for spray coating a device are described, e.g., in U.S. Pat. Nos. 5,464,650 and 5,833,651. Alternatively, a thin film of a therapeutic agent may be molded over the device framework, as described in U.S. Pat. No. 4,866,062.

In general, multiple dipping involves applying several thin layers of the agent, while in liquid form (e.g., a solution, dispersion, or emulsion) of appropriate viscosity, and allowing each liquid layer to dry between successive applications. This method is typical in providing a timed release element of the drug to a device. Drying may be carried out simply by evaporation in air or promoted by heating, including baking or heat flashing, or even osmotic moisture removal, for example, by using a semipermeable membrane. Otherwise, the formation of a solid, adhering layer may be accomplished through chemical or biological transformations occurring on the device surface as described, for example in U.S. Pat. No. 4,548,736 where fibrin is solidified onto the device by carrying out the clotting reaction between fibrinogen and thrombin.

Active flow systems are also possible. For example, U.S. Pat. No. 6,153,252 describes a method using fluid flow or movement through the passages in a perforated medical device to avoid the formation of blockages or bridges. The fluid flow can be created by using a perforated manifold inserted in the device to circulate the coating fluid through the passages or by placing the device on a mandrel or in a small tube that is moved relative to the device during the coating process.

Another possibility for incorporation of a therapeutic agent is through the use of an active material that promotes physical or chemical adsorption. As described in WO 01/68158, an activated form of carbon known as a fullerene can promote the chemical binding of various biological agents (e.g., antibodies) to the surface of the rails 12, 12', 120 and 312 for therapeutic delivery. In the same manner, various materials described previously (e.g., polymeric materials) may be chemically modified, such as by the incorporation of a co-monomer, to introduce functional groups that chemically interact or bind to a given therapeutic agent.

Additionally, a device manufactured from coated strands or coated fabric can be coated with additional layers of active agent after manufacture. The active agent can be coated over the entire device or only on portions thereof.

In yet another embodiment, the active agent may be released simultaneously by all strands or at completely different times or delivery may overlap in time. The release rates of the individual agents or of all agents can be customized for a particular patient or condition using biocompatible polymers and manufacturing methods described above. This would allow the delivery of drug to be optimized to the normal healing processes with the appropriate drug at the right concentration delivered at the desired point in time.

The agents applied in separate layers can be the same agent, different agents with different time releases or different agents intended to be released simultaneously or in successive order. In either instance, barrier layers can cover the different layers of agents. For example, a first barrier layer could cover the rail surface, a first drug layer could be applied on top of the barrier layer and a separation layer applied over the first drug layer. A second drug layer could be applied over the separation layer and then a cover layer could be applied over the second drug layer. More than two drug layers can be applied to the rails. The cover and separation layers can be chosen to provide predetermined and independent time release of the applied agents that they cover.

The different agents discussed above can be applied on different portions of the device. As a result, numerous combinations of agents can be applied to the device.

While preferred embodiments of the present invention have been described, it will be readily appreciated by one of skill in the art that various changes, adaptations, modifications and use of multiple units of the present invention may be made without departing from the spirit of the invention and the scope of the claims.

We claim:

1. A device for scleral depression comprising:
   a solid depressor having a constant thickness of from 2 mm to 8 mm, a height of from 2 mm to 8 mm, a fixed arc length of between 30 and 180 degrees, sized to fit in a fornix; and
   a vertical arm having a length between 6 and 14 mm attached to the depressor; and
   a handle attached to the vertical arm for holding the depressor in position in the fornix of an eye;
   wherein the depressor is shaped to follow a general curvature of a globe of the eye, and wherein the depressor once positioned in the fornix, remains in position until removed and creates a fixed predetermined scleral depression along an arc between 30° and 180° along the fornix of the eye.

2. The device of claim 1 wherein the depressor comprises a first end having a portion sized for fitting in between a sclera and an orbit of the eye.

3. The device of claim 1 wherein the handle is at least partially circular.

4. The device of claim 1 wherein the depressor covers an arc from 120-135 degrees and is from 4-5 mm in thickness.

5. The device of claim 1 which provides for the scleral depression in a temporal, nasal, superior or inferior regions of the eye.

6. The device of claim 1 in which the depressor has a constant or a fixed variable cross section.

7. The device of claim 1 for providing scleral depression by use of an inflatable member.

8. The device of claim 7 in which the inflatable member is a hydrostatically or pneumatically inflatable member which provides semicircular (180° or less) scleral depression.

9. The device of claim 7 in which the inflatable member is selectively inflatable to achieve a range of depth of the scleral depression.

10. The device of claim 7 in which the device is designed to interface with a lid speculum in order to maintain the fixed predetermined scleral depression within the fornix.

11. The device of claim 1 in which a level of depression is varied by interchanging different sized depressors.

12. The device of claim 1 in which the depressor can deliver at least one drug delivered via immediate or controlled release wherein the drug is contained within at least one of the depressor, a surface of the depressor, or a sleeve placed on the depressor.

13. The device of claim 1 wherein the device is integrated into an eyelid speculum.

14. The device of claim 1 further comprising a means for applying light to an outside of a sclera, at, or along areas of depression, such that the light is visible inside the globe of the eye and is used to illuminate anatomical features inside the eye.

15. A kit for hands free scleral depression comprising the device of claim 1 having more than one size of the device.

\* \* \* \* \*